US007557097B2

(12) United States Patent
Sorensen et al.

(10) Patent No.: US 7,557,097 B2
(45) Date of Patent: Jul. 7, 2009

(54) STRUCTURAL, BEHAVIORAL CHARACTERIZATION, AND SYNTHESIS OF ATTRACTANTS FOR MIGRATORY LAMPREY

(75) Inventors: Peter W. Sorensen, St. Paul, MN (US); Thomas R. Hoye, St. Paul, MN (US); Jared M. Fine, St. Paul, MN (US); Vadims Dvornikovs, Minneapolis, MN (US); Jizhou Wang, St. Paul, MN (US); Lance A. Vrieze, Rochester, MN (US)

(73) Assignee: Regents of the University of Minnesota, St. Paul, MN (US)

( * ) Notice: Subject to any disclaimer, the term of this patent is extended or adjusted under 35 U.S.C. 154(b) by 865 days.

(21) Appl. No.: 10/993,802

(22) Filed: Nov. 20, 2004

(65) Prior Publication Data

US 2006/0111333 A1 May 25, 2006

(51) Int. Cl.
*A61K 31/58* (2006.01)
*C07J 41/00* (2006.01)

(52) U.S. Cl. ..................... 514/176; 540/106
(58) Field of Classification Search ............... 540/106; 514/176
See application file for complete search history.

(56) References Cited

U.S. PATENT DOCUMENTS

| 5,541,348 | A | 7/1996 | Ayra et al. |
| 5,620,845 | A | 4/1997 | Gould et al. |
| 5,721,226 | A | 2/1998 | Frye et al. |
| 6,262,283 | B1 | 7/2001 | Kinney et al. |
| 6,610,866 | B2 | 8/2003 | Kinney et al. |
| 2003/0108583 | A1 | 6/2003 | Li et al. |

OTHER PUBLICATIONS

Zhang et al., "Synthesis of Squalamine Uitlizing a Readily Accessible Spermidine Equivalent." J. Organic Chemistry, vol. 63(23), pp. 8599-8603, 1998.*
Collodi, "Large-Scale Production of Petromyzonol Sulfate from Lamprey Liver Cell Cultures and Culture of Sea Lamprey Pituitary Cells," 2000 Project Completion Report of Great Lakes Fishery Commission. Jul. 2000. pp. 1-12.
Schuldt et al, "Portable Trap for Collecting Adult Sea Lampreys," Prof. Fish-Cult. (44)4, Oct. 1982, pp. 220-221.
Hoye, Thomas R. Synthesis Strategies for Bioactive Natural Products, Grant Abstract, Grant No. 1R01GM065597-01, National Institutes of Health (National Institute of General Medical Sciences), Project Start Mar. 1, 2002, Project Stop: Feb. 28, 2006. Retrieved from the Internet on Jul. 30, 2008 at http://crisp.cit.nih.gov/crips/CRISP...
Hoye, Thomas R. Synthesis Strategies for Bioactive Natural Products, Grant Abstract, Grant No. 5R01GM065597-02, National Institutes of Health (National Institute of General Medical Sciences), Project Start Mar. 1, 2002, Project Stop: Feb. 28, 2006. Retrieved from the Internet on Jul. 30, 2008 at http://crisp.cit.nih.gov/crips/CRISP...

Hoye, Thomas R. Synthesis Strategies for Bioactive Natural Products, Grant Abstract, Grant No. 5R01GM065597-03, National Institutes of Health (National Institute of General Medical Sciences), Project Start Mar. 1, 2002, Project Stop: Feb. 28, 2006. Retrieved from the Internet on Jul. 30, 2008 at http://crisp.cit.nih.gov/crips/CRISP...
Hoye, Thomas R. Synthesis Strategies for Bioactive Natural Products, Grant Abstract, Grant No. 5R01GM065597-04, National Institutes of Health (National Institute of General Medical Sciences), Project Start Mar. 1, 2002, Project Stop: Jul. 31, 2007. Retrieved from the Internet on Jul. 30, 2008 at http://crisp.cit.nih.gov/crips/CRISP...
Hoye, Thomas R. Synthesis Strategies for Bioactive Natural Products, Grant Abstract, Grant No. 2R01GM065597-05 A2, National Institutes of Health (National Institute of General Medical Sciences), Project Start Mar. 1, 2002, Project Stop: May 31, 2011. Retrieved from the Internet on Jul. 30, 2008 at http://crisp.cit.nih.gov/crips/CRISP...
Hoye, Thomas R. Synthesis Strategies for Bioactive Natural Products, Grant Abstract, Grant No. 5R01GM065597-06, National Institutes of Health (National Institute of General Medical Sciences), Project Start Mar. 1, 2002, Project Stop: May 31, 2011. Retrieved from the Internet on Jul. 3, 2008 at http://crisp.cit.nih.gov/crips/CRISP...
Gao et al., "Synthesis of Cyclocholates and Derivatives," *Syn. Comm.*, 1997;27(5):757-776.
Joyce et al., "Bile Acids. LXXIII. Synthesis of Analogs of 7α-Hydroxy-4-Cholesten-3-One as Substrates for Hepatic Steroid 12α-Hydroxylase," *Steroids*, Jul. 1984;44(1):95-101.
Morris et al., "A trap for catching adult lampreys (Petromyzonidae) in running water," *J. Fish Biol.*, 1987;31:513-516.
Nicolaou et al., "Iodine(v) Reagents in Organic Synthesis. Part. 4. o-Iodoxybenzoic Acid as a Chemospecific Tool for Single Electron Transfer-Based Oxidation Processes," *J. Am. Chem. Soc.*, 2002;124(10):2245-2258.
Nilsson et al., "Neurosteroid Analogues. 6. The Synthesis and $GABA_A$ Receptor Pharmacology of Enantiomers of Dehydroepiandrosterone Sulfate, Pregnenolone Sulfate, and (3α,5β)-3-Hydroxypregnan-20-one Sulfate," *J. Med Chem.*, 1998;41:2604-2613.
Purvis et al., "Response of Spawning-Phase Sea Lampreys (Petromyzon marinus) to a Lighted Trap," Great Lakes Fishery Commission, Technical Report No. 42, 1981-82;15-25.
Shu et al., "The synthesis of spermine analogs of the shark aminosterol squalamine," *Steroids*, 2002;67:291-304.
Sorensen et al., "Chemoreception," *The Physiology of Fishes*, 2nd Ed., Evans, Ed., 1998, Boca Raton, FL, 375-405.
Tochtrop et al., "A Simple Efficient Synthesis of [23,24]-$^{13}C_2$-Labeled Bile Salts as NMR Probes of Protein-Ligand Interactions," *Bio. Med. Chem. Letters*, 2002;12:433-435.
Watson et al., "An enantioselective synthesis of sulphonamide hydroxamic acids as matrix metalloproteinase inhibitors," *Tetrahedon Letters*, 2002;43:683-685.
Zhang et al., "A Concise and Stereoselective Synthesis of Squalamine," *Organic Letters*, 2003;5(18):3257-3259.

(Continued)

*Primary Examiner*—Barbara P Badio
(74) *Attorney, Agent, or Firm*—Mueting Raasch & Gebhardt, P.A.

(57) ABSTRACT

Compounds that function as lamprey attractants and methods.

5 Claims, 4 Drawing Sheets

OTHER PUBLICATIONS

Li et al., "The Olfactory System of Migratory Adult Sea Lamprey (*Petromyzon marinus*) is Specifically and Acutely Sensitive to Unique Bile Acids Released by Conspecific Larvae," *J. Gen. Physiol.*, 1995;105(5):569-587.

Li et al., "Highly independent olfactory receptor sites for naturally occurring bile acids in the sea lamprey, *Petromyzon marinus*," *J. Comp. Physiol. A*, 1997;180:429-438.

Polkinghorne et al., "Larval sea lamprey release two unique bile acids** to the water at a rate sufficient to produce detectable riverine pheromonal plumes," *Fish Physiol. Biochem.*, 2001;24:15-30.

Schneider et al., "Inhibitory Potency of Lithocholic Acid Analogs and Other Bile Acids on Glucuronosyltransferase Activity in a Colon Cancer Cell Line", *Bioorg & Med Chem Lett*, 1996:6(6):637-642.

Applegate, "Natural History of the Sea Lamprey, *Petromyzon marinus*, in Michigan," *Spec. Sci. Rep., Fisheries, No. 55*, 1950, cover page, and table of contents only (4 pgs).

Bjerselius et al., "Direct behavioral evidence that unique bile acids released by larval sea lamprey (*Petromyzon marinus*) function as a migratory pheromone," *Can J. Fish. Aquat. Sci.*, 2000;57:557-569.

Christie et al., "Sea Lamprey International Symposium (SLIS II): Advances in the Integrated Management of Sea Lamprey in the Great Lakes," *J. Great Lakes Res.*, 2003;29(Suppl 1):1-14.

Close et al., "The Ecological and Cultural Importance of a Species at Risk of Extinction, Pacific Lamprey," *Fisheries*, 2002;27(7):19-25.

De Marino et al., "Starfish Saponins. 55.[1] Isolation, Structure Elucidation, and Biological Activity of the Steroid Oligoglycosides from an Antarctic Starfish of the Family Asteriidae," *J. Nat. Prod.*, 1998;61(11):1319-1327.

Fine et al., "Partial identification of a multi-component migratory pheromone used by the sea lamprey," oral presentation, Chemical Signals in Vertebrates, Oregon St. University, Jul. 29, 2003, abstract and slides, 18 pgs.

Fine et al., "Identification of a migratory pheromone used by the sea lamprey," oral presentation, St. Cloud, MN, Dec. 2003, PowerPoint presentation, 8 pgs.

Fine et al., "Chemical fractionation demonstrates that the sea lamprey migratory pheromone is comprised of several bile acid-like compounds," Press Information Packet, AChems meeting, Sarasota, FL, Apr. 2004, 2 pgs.

Fine et al., "Chemical Fractionation Demonstrates that the Sea Lamprey Migratory Pheromone is Comprised of Several Bile Acid-like Compounds," AChems meeting, Sarasota, FL, Apr. 2004, meeting abstract and poster, 2 pgs.

Fine et al., "Chemical fractionation demonstrates that the sea lamprey migratory pheromone is comprised of several bile acid-like compounds," Minnesota Chapter of the American Fisheries Society, Apr. 15-18, 2004, St. Cloud, MN, meeting abstract and poster, 2 pgs.

Fine et al., "Bio-assay guided fractionation demonstrates that the sea lamprey migratory pheromone is a mixture of at least three sulfated steroids," International Society for Chemical Ecology, Jul. 24-28, 2004, Ottawa, CA, abstract and meeting poster, 2 pgs.

Fine et al., "Evidence that Petromyzontid Lampreys Employ a Common Migratory Pheromone that is Partially Comprised of Bile Acids," *Journal of Chemical Ecology*, 2004;30(11):2085-2105.

Fine et al., "Biologically Relevant Concentrations of Petromyzonal Sulfate, a Component of the Sea Lamprey Migratory Pheromone, Measured in Stream Water," *Journal of Chemical Ecology*, Rapid Communication, 2005;1-6.

Hasler et al., "Olfactory Imprinting and Homing in Salmon," *Zoophysiology*, vol. 14, Springer-Verlag, New York, 1983, cover page, pp. 3-12.

Haselwood et al., "Comparative Studies of Bile Salts: Bile Salts of the Lamprey *Petromyzon marinus* L.," *Biochem. J.*, 1969;114:179-184.

Higashibayashi et al., "Universal NMR Databases for Contiguous Polyols," *J. Am. Chem. Soc.*, 2003;125:14379-14393.

Hoye, "The Latest Trends in Organic Synthesis in One Minnesota Lab: NMR Tricks for Everyone (No-D and More)," abstract from conference booklet, Brock University, St. Catharines, Ontario, CA, Aug. 13, 2004, 1 pg.

Hoye, "The Latest Trends in Organic Synthesis in One Minnesota Lab: NMR Tricks for Everyone (and Everyday Use)," Brock University, St. Catharines, Ontario, CA, Aug. 13, 2004, PowerPoint presentation, 18 pgs.

Iorizzi et al., "Polyoxygenated Marine Steroids from the Deep Water Starfish *Styracaster caroli*," *J. Nat Prod.*, 1994;57(10):1361-1373.

Iorizzi et al., "Chemical and Biological Investigation of the Polar Constituents of the Starfish *Luidia clathrata*, Collected in the Gulf of Mexico," *J. Nat. Prod.*, 1995;58(5):653-671.

Karlson et al., "Pheromones': a New Term for a Class of Biologically Active Substances," *Nature*, 1959;183:55-56.

Kleerekoper, "The Sense Organs," *The Biology of Lampreys*, London, England, 1972, cover page, pp. 373-404.

Li et al., "The Olfactory System of Migratory Adult Sea Lamprey (*Petromyzon marinus*) is Specifically and Acutely Sensitive to Unique Bile Acids Released by Conspecific Larvae," *J. Gen. Physiol.*, 1995;105(5):569-587.

Li et al., "Highly independent olfactory receptor sites for naturally occurring bile acids in the sea lamprey, *Petromyzon marinus*," *J. Comp. Physiol. A*, 1997;180:429-438.

Li et al., "Bile Acid Secreted by Male Sea Lamprey That Acts as a Sex Pheromone," *Science*, 2002;296:138-141.

Moore et al., "Changes in Spawning Runs of Sea Lamprey (*Petromyzon marinus*) in Selected Streams of Lake Superior after Chemical Control," *Can. J. Fish. Aquat. Sci.*, 1980;37:1851-1860.

Moore et al., "Squalamine: An aminosterol antibiotic from the shark," *Proc. Natl. Acad. Sci. USA*, 1993;90:1354-1358.

Polkinghorne et al., "Larval sea lamprey release two unique bile acids** to the water at a rate sufficient to produce detectable riverine pheromonal plumes," *Fish Physiol. Biochem.*, 2001;24:15-30.

Rao et al., "Aminosterols from the Dogfish Shark *Squalus acanthias*," *J. Nat. Prod.*, 2000;63:631-635.

Sorensen et al., "Pheromones," *The Corsini Encyclopedia of Psychology and Behavioral Science*, 2001;3:1194-1195.

Sorensen et al., "Sea lamprey employ a multi-component migratory pheromone," oral presentation, Sixth International Symposium on Fish Reproductive Physiology, Mie, Japan, Jul. 5, 2003, slides, 10 pgs.

Sorensen et al., "A multi-component migratory pheromone in the sea lamprey," *Fish Physiology and Biochemistry*, 2003;28:253-257.

Sorensen et al., "The Chemical Ecology and Potential Application of the Sea Lamprey Migratory Pheromone," *J. Great Lakes Res.*, 2003;29(Supp 1):66-84.

Teeter, "Pheromone Communication in Sea Lampreys (*Petromyzon marinus*): Implications for Population Management," *Can J. Fish. Aquat. Sci.*, 1980;37:2123-2132.

Twohey et al., "Possible Applications of Pheromones in an Integrated Sea Lamprey Management Program," *J. Great Lakes Res.*, 2003;29(Suppl):794-800.

Vrieze et al., "Laboratory assessment of the role of a larval pheromone and natural stream odor in spawning stream localization by migratory sea lamprey (*Petromyzon marinus*)," *Canadian Journal of Fisheries and Aquatic Science*, 2001;58(12):2374-2385.

Wabnitz et al., "Aquatic sex pheromone from a male tree frog," *Nature*, 1999;401:444-445.

Wyatt, "Animals in a chemical world," *Pheromones and Animal Behaviour; Communication by Smell and Taste*, Cambridge University Press, Cambridge, UK, 2003;cover page, title page, pp. 1-22.

Sorensen et al., "*Luring Lampreys: Assessing the Feasibility of Using Odorants to Control Sea Lamprey in the Great Lakes*", Great Lakes Fishery Commission 1993 Project Completion Report, Great Lakes Fishery Commission, Marine-on-Croix, Minnesota, Oct. 29-31, 1993, title page and pp. 1-110.

Sorensen et al., "*Determining Why the Sea Lamprey Olfactory System is Extremely Sensitive to Bile Acids: Are Bile Acids Pheromones?*", Great Lakes Fishery Commission Research Completion Report, Mar. 18, 1994, title page and pp. 1-31.

Sorensen et al., "*Evaluating the seasonality of olfactory function of migratory adult sea lamprey and the distribution of water-borne lamprey bile acids in the Great Lakes to determine whether bile acids function as the lamprey migratory pheromone*", Great Lakes Fishery Commission Project Completion Report, Mar. 1996, 30 pgs.

Sorensen, "*The Influence of Pheromones on the Distributional Biology of Adult Sea Lamprey*", Great Lakes Fishery Commission Project Completion Report, Feb. 1998, 23 pgs.

Sorensen, "*Determining the Sources and Complete Chemical Composition of the Lamprey Larval Pheromone, and Assessing the Merit of Measuring One of its Principal Components in River Waters—Phase I*", Great Lakes Fishery Commission 2000 Project Completion Report, Mar. 2000, 42 pgs.

Sorensen, "*Determining the Sources and Complete Chemical Composition of the Lamprey Larval Pheromone, and Assessing the Merit of Measuring One of its Principal Components in River Waters—Phase II*", Great Lakes Fishery Commission 2001 Project Completion Report, Mar. 2001, 24 pgs.

Sorensen, "*A first step towards developing a field test to determine whether a larval pheromone can be used in sea lamprey control: ascertaining its effects on adult behavior in a lake and characterizing the complete pheromone*", Great Lakes Fishery Commission 2003 Project Completion Report, Mar. 2003, 26 pgs.

Sorensen, "*Identifying and producing the sea lamprey migratory pheromone*", Great Lakes Fishery Commission 2004 Project Completion Report, Apr. 2004, 14 pgs.

\* cited by examiner

Petromyzonol sulfate

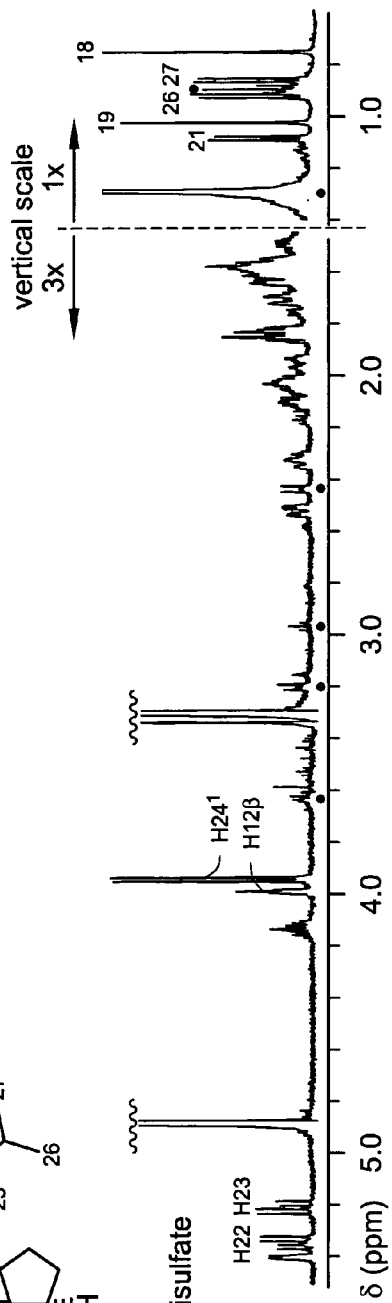
Fig. 3B Petromyzosterol disulfate
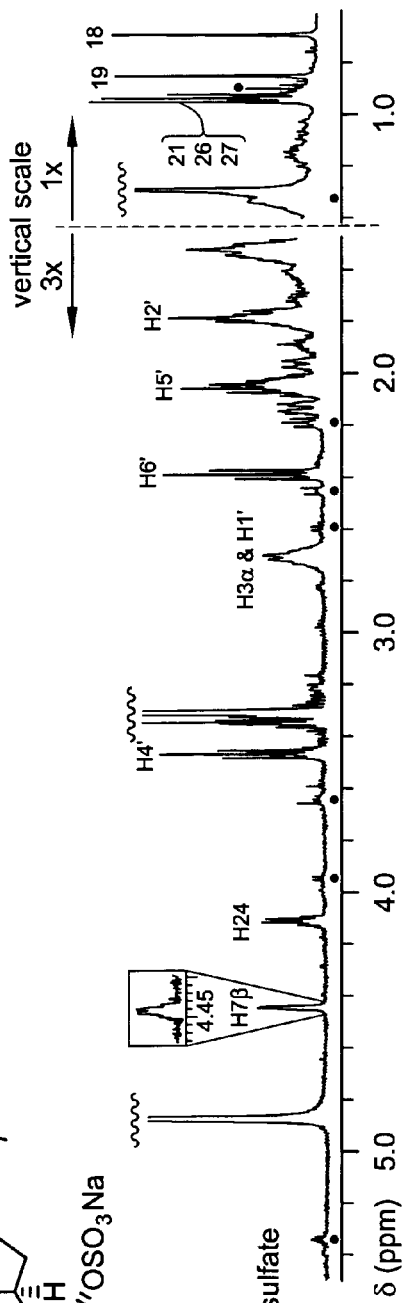
Fig. 3C Petromyzonamine disulfate

STRUCTURAL, BEHAVIORAL CHARACTERIZATION, AND SYNTHESIS OF ATTRACTANTS FOR MIGRATORY LAMPREY

STATEMENT OF GOVERNMENT RIGHTS

This work was supported in part by the National Institutes of Health under Grant Number GM65597. The government may have certain rights in the invention.

BACKGROUND

Hundreds of aquatic vertebrates perform extensive migrations between specific locales or habitats. Although it is well known that many of these directed movements are guided by chemical cues, their specific identities have not yet been clearly established. Nevertheless, two distinct processes have been elucidated. In one, juveniles learn complex suites of compounds in their natal environment which they later recognize when they re-encounter them as migratory adults (e.g., salmon, sea turtles). In the other, migrating individuals instinctively recognize cues that have some inherent ecological relevance (e.g., eels, lamprey). Chemicals released by members of the same species (i.e., pheromones) frequently play a critical role in the later process, likely because habitat quality and species abundance are typically correlated. Herein, we define pheromones (which have historically been defined in many ways (Sorensen and Wyatt *Corsini Encyclopedia of Psychology and Behavioral Science*, Wiley (2001)) as "substances that are secreted to the outside by an individual and received by a second individual of the same species, in which they release a specific reaction, for example, a definite behaviour or developmental process" (Karlson and Luscher, *Nature*, 183: 55-56 (1959)).

The sea lamprey is an appropriate and fascinating species to investigate pheromonally mediated migration. One of the few survivors from early vertebrate evolution, it possesses an exceptionally large olfactory system that it employs to mediate all aspects of its life. The sea lamprey is also a destructive pest in the Finger Lakes of New York and New England (Lake Champlain, Lake Oneida, and Lake Cayauga in particular) and in the Laurentian Great Lakes. Sea lampreys invaded these systems in the early 20th century where they quickly established themselves and drove many fishes to extinction. Although the fisheries of the Great Lakes have partially recovered since the implementation of a control program based on larval poisons, new and better means to control sea lamprey are sought. Their migratory life history offers specific opportunities for control. Adult sea lamprey spawn in freshwater streams where its eyeless larvae then reside for 3-20 years before metamorphosing into a parasitic phase that migrates downstream to oceans/large lakes to find hosts. Parasitic lamprey are transported by hosts great distances before they mature and seek out spawning streams, which they then enter to find mates, spawn, and die. Studies of free-ranging adults demonstrate that stream finding is guided by olfactory cues. Further, fisheries catch data have long suggested that these cues originate from stream-resident larvae (i.e., pheromones) since adults do not return to natal streams but instead exhibit strong biases for streams containing larvae (Vrieze and Sorensen, *Can. J. Fish Aquat. Sci.*, 58:2374-2385 (2001); Sorensen et al. *J Great Lakes Res*, 29 (Supplement 1): 66-84 (2003)).

More direct evidence of pheromonal attractants results from studies showing larval holding water to be remarkably attractive (a 1 g larva activates over 300 liters of water an hour) and to alter the choices of adults for stream waters (Vrieze and Sorensen, *Can. J. Fish Aquat. Sci.*, 58:2374-2385 (2001)). Efforts to identify structural aspects of the lamprey migratory pheromone began a decade ago when it was hypothesized that a unique bile acid, petromyzonol sulfate (1) already known to be produced by larval lamprey (Haslewood et al., *J. Biochem.*, 114, 179-184 (1969)), might be released to the water to function as a pheromone (Sorensen et al., *J. Great Lakes Res.*, 29 (Supplement 1):66-84 (2003)). It was subsequently demonstrated that larval lamprey release significant quantities of 1, along with lesser quantities of its likely precursor, allocholic acid (ACA), and that the adult lamprey olfactory system detects these products with high specificity at $10^{-12}$ and $10^{-11}$ Molar (M) (Polkinghorne et al., *Fish Physiol. Biochem.*, 24, 15-30 (2001); Li et al., *J. Gen. Physiol.*, 105, 569-589 (1995)); and Li et al., *J. Comp Physiol. A.*, 180, 429-438 (1997)). Behavioural tests using a large maze and natural waters also found a mixture of 1 and ACA to be attractive (Vrieze et al., *Can. J. Fish. Aquat. Sci.*, 58, 2374-2385 (2001)), while electrospray ionization mass spectrometry (ESI-MS) identified 1 (but not ACA) in river water at concentrations ranging up to $10^{-11}$ M. However, these studies also found responses to 1 and/or ACA to be weaker than those to larval holding water, suggesting that the larval pheromone, like most insect pheromones, is a complex mixture.

SUMMARY

The present invention provides compounds that function as attractants for lamprey, particularly sea lamprey, whether adult or larval lamprey. More particularly, these compounds have been identified as pheromones that guide migratory adults of lamprey, particularly sea lamprey, to their spawning grounds, for example. They are steroids and are remarkable compounds because of their chemical novelty and great olfactory potency. Such compounds preferably complement and enhance the actions of petromyzonol sulfate (1).

The compounds of the present invention can be used alone or in combination with each other, or in combination with other compounds (e.g., petromyzonol sulfate (1), bile acids, or bile acid derivatives). Preferably, they are used in a blend with each other and optionally with petromyzonol sulfate (1).

The discovery and structural elucidation of these pheromones opens new doors for the use of pheromones, both to control the sea lamprey in the Great Lakes and, perhaps, to conserve native lamprey species found in coastal regions of the Atlantic and Pacific Oceans, for example.

In one embodiment, there is provided an isolated or chemically synthesized compound having the formula (Formula I):

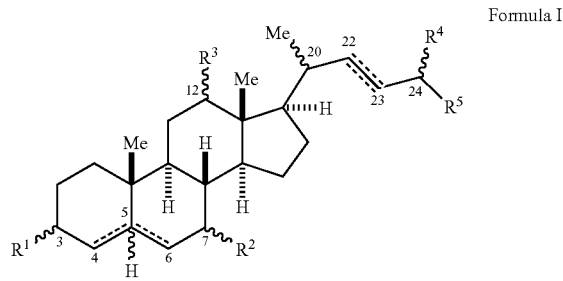

Formula I wherein:

$R^1$, $R^2$, and $R^3$ are independently selected from the group consisting of H, —OH, —OSO$_3$M, and —OPO$_3$M$_2$;

$R^4$ is H, a branched or unbranched alkyl, a branched or unbranched alkenyl, a cycloalkyl, an aryl, or a heteroaryl;

$R^5$ is H, —OH, —O—$R^6$, —$OSO_3M$, —$OPO_3M_2$, —$CH_2OH$, —$CH_2OSO_3M$, or —$CH_2OPO_3M_2$;

$R^6$ is a branched or unbranched alkyl;

M is hydrogen or a counterion;

 represents a single or double carbon-carbon bond between C4 and C5 or C5 and C6;

 represents a single, double, or a triple carbon-carbon bond between C22 and C23; and

 at C3, C5, C7, C12, C20, and C24 represents a bond to the attached substituent that is either in front of (β) or behind (α) the plane of the paper, and defines the R or S absolute configuration of the carbon atom that bears the attached substituent;

with the following provisos:
the compound includes at least one sulfur or phosphorous atom;
when $R^4$ is isopropyl, $R^5$ is not H; or when $R^4$ is H, $R^5$ is not —$OSO_3M$; or when $R^4$ is —$CH_3$, $R^4$ is not H; and
when $R^5$ is isopropyl, and $R^4$ is —OH or —$OSO_3M$, then $R^3$ is —OH or —$OSO_3M$.

In a particularly preferred embodiment of Formula I of the present invention, there is provided an isolated or chemically synthesized compound having the formula:

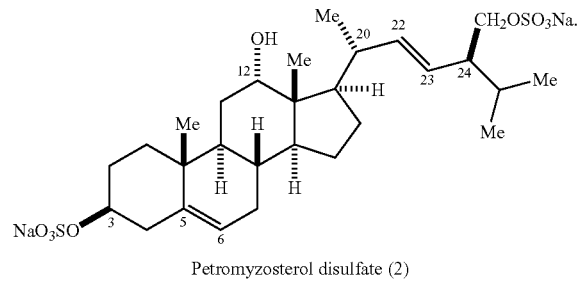

Petromyzosterol disulfate (2)

In one embodiment, there is provided an isolated or chemically synthesized compound having the formula (Formula II):

Formula II

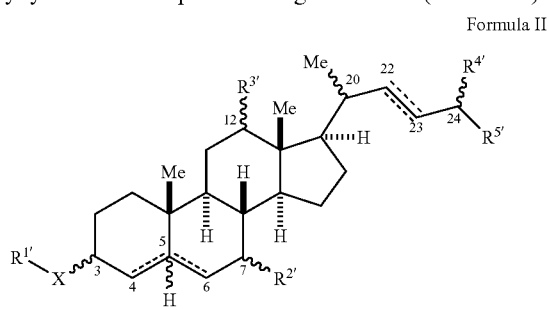

wherein:

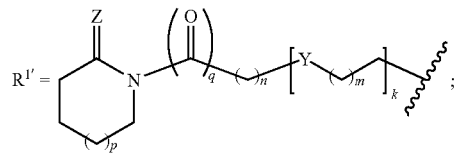

$R^{2\prime}$ and $R^{3\prime}$ are independently selected from the group consisting of H, —OH, —$OSO_3M$, and —$OPO_3M_2$;

$R^{4\prime}$ is H, a branched or unbranched alkyl, a branched or unbranched alkenyl, a cycloalkyl, an aryl, a heteroaryl, —$(CH_2)_rOH$, —$(CH_2)_rOSO_3M$, or —$(CH_2)_rOPO_3M_2$;

$R^{5\prime}$ is H, —OH, —O—$R^{6\prime}$, —$OSO_3M$, —$OPO_3M_2$, —$CH_2OH$, —$CH_2OSO_3M$, or —$CH_2OPO_3M_2$;

M is hydrogen or a counterion;

$R^{6\prime}$ is a branched or unbranched alkyl;

X is —N(H)—, —C(O)N(H)—, —C(O)N($R^{7\prime}$)—, —N($R^{7\prime}$)—, or —O—;

$R^{7\prime}$ is a branched or unbranched alkyl or a cycloalkyl;

Y is —O—, —N(H)—, or —N($R^{8\prime}$)—;

$R^{8\prime}$ is a branched or unbranched alkyl or a cycloalkyl;

Z is O or $H_2$;

 represents a single or double carbon-carbon bond between C4 and C5 or C5 and C6;

 represents a single, double, or a triple carbon-carbon bond between C22 and C23;

 at C3, C5, C7, C12, C20, and C24 represents a bond to the attached substituent that is either in front of (β) or behind (α) the plane of the paper, and defines the R or S absolute configuration of the carbon atom that bears the attached substituent;

m is 1, 2, 3, or 4;
n is 1, 2, 3, or 4;
k is 0, 1, or 2;
p is 0, 1, or 2;
q is 0 or 1; and
r is 0, 1, 2, or 3;
with the proviso that $R^{1\prime}$ is not 2-(N-pyrrolidino)ethylamino.

In a particularly preferred embodiment of Formula II of the present invention, there is provided an isolated or chemically synthesized compound having the formula:

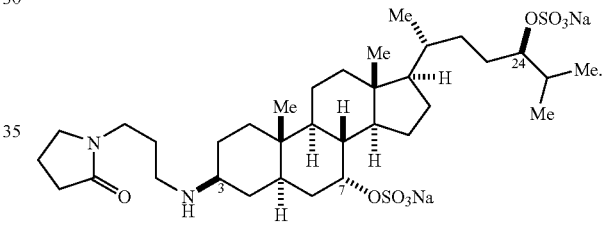

Petromyzonamine disulfate (3)

In other embodiments, there is provided a solid form of a compound having the above Formula I, and preferably a solid form of petromyzosterol disulfate (2).

In other embodiments, there is provided a solid form of a compound having the above Formula II, and preferably a solid form of petromyzonamine disulfate (3).

In another embodiment, there is provided a lamprey attractant composition including a compound of Formula I (preferably, petromyzosterol disulfate (2)), Formula II (preferably, petromyzonamine disulfate (3)), or combinations thereof, and a carrier. Preferably, such lamprey attractant compositions include petromyzonol sulfate (1), which has the following structure:

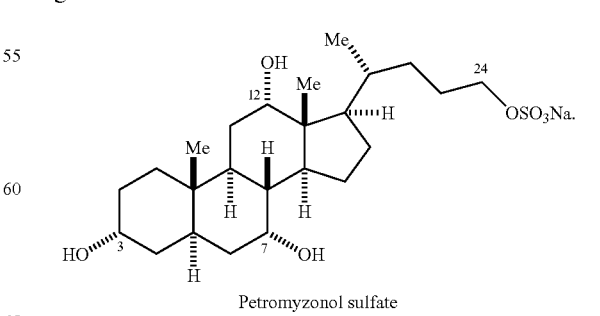

Petromyzonol sulfate

In certain embodiments, a lamprey attractant composition includes at least one compound of Formula I and at least one compound of Formula II, and preferably, petromyzonol sulfate (1). In a preferred embodiment, the lamprey attractant composition includes petromyzosterol disulfate (2), petromyzonamine disulfate (3), petromyzonol sulfate (1), and a carrier.

In other embodiments, there is provided a lamprey attractant composition that preferably includes at least 1 wt-% (more preferably, at least 10 wt-%) of an attractant, wherein the attractant is a compound of Formula I, a compound of Formula II, or a combination of compounds of Formula I and Formula II.

In other embodiments, there is provided a lamprey attractant composition that includes at least $10^{-5}$ M of an attractant, wherein the attractant is a compound of Formula I, a compound of Formula II, or a combination of compounds of Formula I and Formula II.

In other embodiments, there is provided a lamprey trap or barrier that includes a compound of Formula I, a compound of Formula II, or a combination of compounds of Formula I and Formula II.

The present invention also provides methods of using and methods of making (e.g., isolating such as by extraction) compounds described herein.

In one embodiment, a method of attracting lamprey to a specific location is provided. The method includes introducing an isolated or chemically synthesized compound of Formula I, an isolated or chemically synthesized compound of Formula II, or a combination thereof, into a body of water to attract the lamprey to the site of compound introduction. Preferably, the method further includes harvesting the lamprey from the body of water. If the chosen site is one that does not permit the survival of young lamprey or does not allow adults to reproduce, this is not necessary.

In one embodiment, a method of disrupting lamprey behavior is provided. The method includes introducing an isolated or chemically synthesized compound of Formula I, an isolated or chemically synthesized compound of Formula II, or a combination thereof into a body of water in an amount effective to disrupt lamprey behavior. Preferably, disrupting lamprey behavior includes repelling lamprey, promoting behavioral confusion, reducing lamprey reproduction, disrupting upstream movement, or combinations thereof.

The present invention also provides a method of extracting a compound of Formula I and/or a compound of Formula II from water, the method comprising contacting the water with an extraction resin. Typically, the water is a sample of a stream or lamprey holding water. The extraction resin can be a porous polymeric adsorbent or a reverse phase silica gel resin, for example.

The compounds of the present invention are also useful for assessing the population of larval lamprey in a body of water. Thus, the present invention provides such a method that involves measuring the amount of a compound of Formula I and/or a compound of Formula II. Measuring the amount of these compounds can be done using mass spectometry and/or ELISA.

The term "isolated" means a compound that is removed from its natural environment.

The terms "comprises" and variations thereof do not have a limiting meaning where these terms appear in the description and claims.

As used herein, "a," "an," "the," "at least one," and "one or more" are used interchangeably. Thus, for example, a composition that comprises "a" compound of a recited structure can be interpreted to mean that the composition includes "one or more" compounds of the recited structure. Furthermore, a "composition" as used herein can consist of just one compound of the recited structure without any other components.

When a group (or substituent or variable) is present more than once in any Formula described herein, each group (or substituent or variable) is independently selected, whether explicitly stated or not.

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS

Figure 1A:
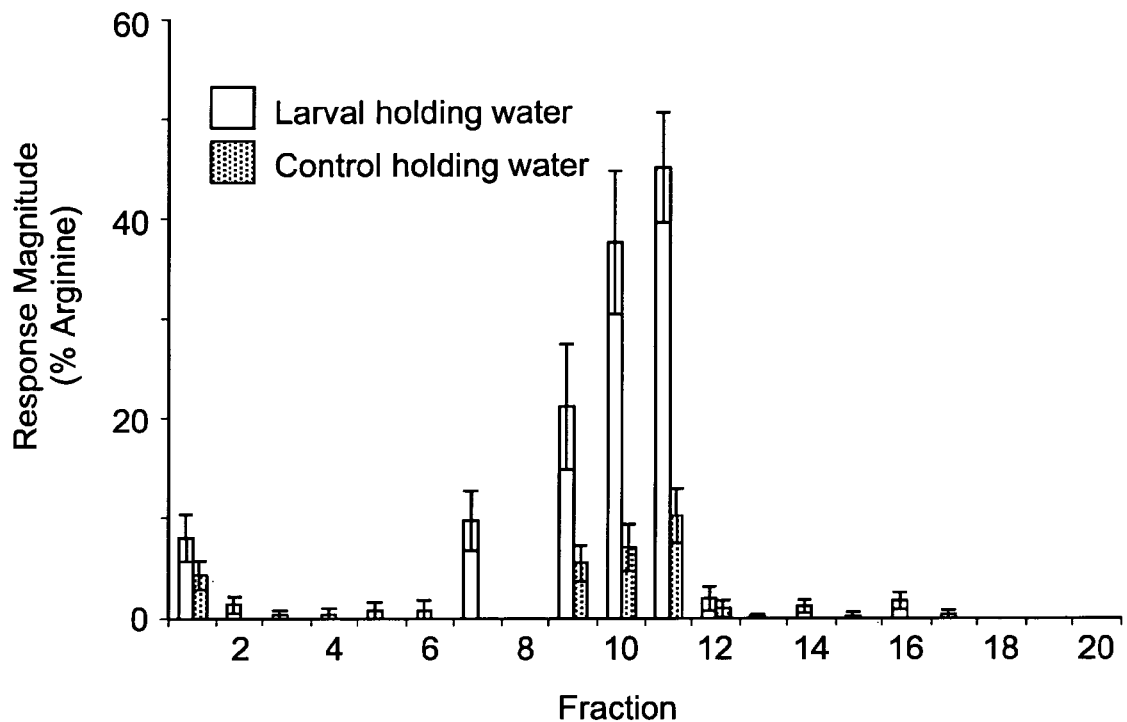
FIG. 1. Olfactory and behavioral responses to fractionated larval waters. (a) Average EOG responses (±standard error) recorded from migratory adult sea lamprey (n=5) to fractionated sea lamprey holding water and control water from tanks lacking larvae. (b) Mean percent time (±95% confidence intervals) spent by adult sea lampreys in HPLC fractions 9, 10, and 11 when tested directly against larval extract in the behavior maze (N=14 trials of 4 lampreys).

The present invention provides compounds that function as lamprey attractants, particularly sea lamprey attractants. These compounds can be used to guide migratory adults of lamprey, particularly sea lamprey, to their spawning grounds, for example. Other uses of such compounds are also envisioned and discussed herein.

The compounds of the present invention can be synthesized using standard chemical techniques. Additionally, certain specific compounds of the present invention can be extracted or otherwise isolated from sea lamprey larvae, or sea lamprey larvae holding water, for example.

In one embodiment, the present invention provides a compound having the formula (Formula I):

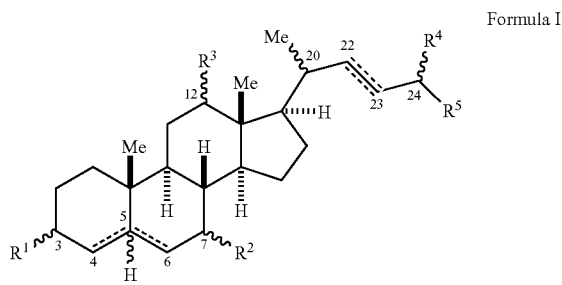

Formula I wherein:

$R^1$, $R^2$, and $R^3$ are independently selected from the group consisting of H, —OH, —OSO$_3$M, and —OPO$_3$M$_2$;

$R^4$ is H, a branched or unbranched alkyl, a branched or unbranched alkenyl, a cycloalkyl, an aryl, or a heteroaryl;

$R^5$ is H, —OH, —O—R$^6$, —OSO$_3$M, —OPO$_3$M$_2$, —CH$_2$OH, —CH$_2$OSO$_3$M, or —CH$_2$OPO$_3$M$_2$;

$R^6$ is a branched or unbranched alkyl;

M is hydrogen or a counterion;

⟿ represents a single or double carbon-carbon bond between C4 and C5 or C5 and C6;

⟿ represents a single, double, or a triple carbon-carbon bond between C22 and C23; and ⟩ at C3, C5, C7, C12, C20, and C24 represents a bond to the attached substituent that is either in front of (β) or behind (α) the plane of the paper, and defines the R or S absolute configuration of the carbon atom that bears the attached substituent;

with the following provisos:

the compound includes at least one sulfur or phosphorous atom;

when $R^4$ is isopropyl, $R^5$ is not H; or when $R^4$ is H, $R^5$ is not —OSO$_3$M; or when $R^4$ is —CH$_3$, $R^4$ is not H; and when $R^5$ is isopropyl, and $R^4$ is —OH or —OSO$_3$M, then $R^3$ is —OH or —OSO$_3$M.

In the compounds of Formula I, the organic groups (e.g., alkyls, alkenyls, cycloalkyls, aryls, heteroaryls) are of a size that does not disrupt the function of the compound.

In certain preferred embodiments of Formula I, $R^1$, $R^2$, and $R^3$ are independently selected from the group consisting of H, —OH, —OSO$_3$M, and —OPO$_3$M$_2$. In certain more preferred embodiments of Formula I, at least one of $R^1$, $R^2$, and $R^3$ is —OH or —OSO$_3$M. In certain even more preferred embodiments of Formula I, $R^1$ is —OH or —OSO$_3$M.

In certain preferred embodiments of Formula I, $R^4$ is H, a branched or unbranched alkyl, a branched or unbranched alkenyl (having one or more carbon-carbon double bonds), a cycloalkyl, an aryl, or a heteroaryl. In certain more preferred embodiments of Formula I, $R^4$ is H, a branched or unbranched alkyl having six carbons or less, a branched or unbranched alkenyl (having one or more carbon-carbon double bonds) having six carbons or less, a cycloalkyl having six carbons or less, an aryl having ten carbons or less, or a heteroaryl having five carbons or less. In certain even more preferred embodiments of Formula I, $R^4$ is H, a branched or unbranched alkyl having six carbons or less, or a heteroaryl having five carbons or less.

In certain preferred embodiments of Formula I, $R^5$ is H, —OH, —O—R$^6$, —OSO$_3$M, —OPO$_3$M$_2$, —CH$_2$OH, —CH$_2$OSO$_3$M, or —CH$_2$OPO$_3$M$_2$. In certain more preferred embodiments of Formula I, $R^5$ is H, —OH, —O—R$^6$, —OSO$_3$M, —CH$_2$OH, or —CH$_2$OSO$_3$M. In certain even more preferred embodiments of Formula I, $R^5$ is —OH, —OSO$_3$M, —CH$_2$OH, or —CH$_2$OSO$_3$M.

In certain preferred embodiments of Formula I, $R^6$ is a branched or unbranched alkyl having five carbons or less. In certain more preferred embodiments of Formula I, $R^6$ is an unbranched alkyl having five carbons or less.

In certain preferred embodiments of Formula I, M is H or a counterion, and more particularly, H, Na, K, Ca, NH$_4$, or R$_4$N, wherein each R is independently a branched or unbranched alkyl (preferably, unbranched) having four carbons or less. In certain more preferred embodiments of Formula I, M is a Na, K, or NH$_4$ counterion. In certain even more preferred embodiments of Formula I, M is a Na counterion.

In certain preferred embodiments of Formula I, $R^1$ is —OH or —OSO$_3$M; $R^4$ is H, a branched or unbranched alkyl having six carbons or less, or a heteroaryl having five carbons or less; $R^5$ is —OH, —OSO$_3$M, —CH$_2$OH, or —CH$_2$OSO$_3$M; and M is a Na, K, or NH$_4$ counterion.

In certain preferred embodiments of Formula I, at least one of $R^1$, $R^2$, and $R^3$ is —OH or —OSO$_3$M; $R^4$ is H, a branched or unbranched alkyl or alkenyl having six carbons or less; $R^5$ is —OH, —OSO$_3$M, —CH$_2$OH, or —CH$_2$OSO$_3$M; and M is a Na, K, or NH$_4$ counterion.

In certain more preferred embodiments of Formula I, at least one of $R^1$, $R^2$, and $R^3$ is —OH or —OSO$_3$M; $R^4$ is H, a branched or unbranched alkyl having six carbons or less; $R^5$ is —OH, —OSO$_3$M, —CH$_2$OH, or —CH$_2$OSO$_3$M; and M is a Na counterion.

In certain preferred embodiments of Formula I, $R^1$ is —OH or —OSO$_3$M; $R^4$ is H or a branched or unbranched alkyl having six carbons or less; $R^5$ is —OH, —OSO$_3$M, —CH$_2$OH, or —OSO$_3$M; and M is a Na counterion.

In certain preferred embodiments of Formula I, the compound includes at least one sulfur or phosphorous atom.

In certain preferred embodiments of Formula I, when $R^4$ is isopropyl, $R^5$ is not H; or when $R^4$ is H, $R^5$ is not —OSO$_3$M; or when $R^4$ is —CH$_3$, $R^4$ is not H.

In certain preferred embodiments of Formula I, when $R^5$ is isopropyl, and $R^4$ is —OH or —OSO$_3$M, then $R^3$ is —OH or —OSO$_3$M.

A particularly preferred compound of Formula I is petromyzosterol disulfate (2), which has the following structure:

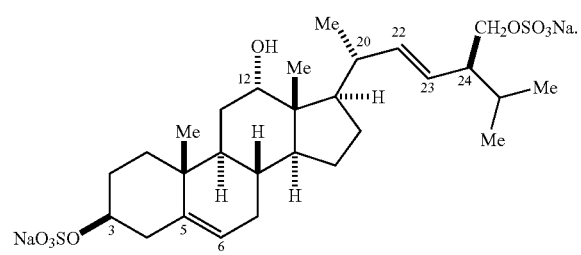

Petromyzosterol disulfate (2)

In another embodiment, the present invention provides a compound having the formula (Formula II):

Formula II

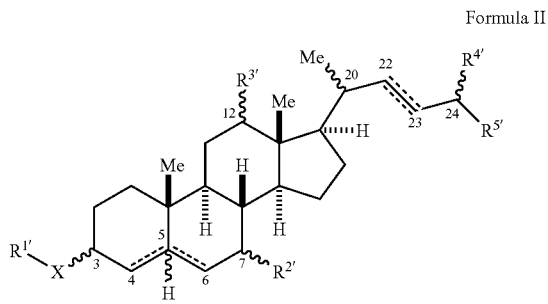

wherein:

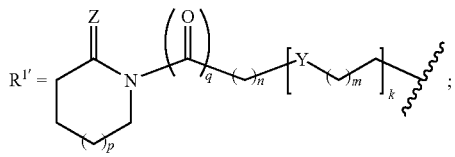

$R^{2'}$ and $R^{3'}$ are independently selected from the group consisting of H, —OH, —OSO$_3$M, and —OPO$_3$M$_2$;
$R^{4'}$ is H, a branched or unbranched alkyl, a branched or unbranched alkenyl, a cycloalkyl, an aryl, a heteroaryl, —(CH$_2$)$_r$OH, —(CH$_2$)$_r$OSO$_3$M, or —(CH$_2$)$_r$OPO$_3$M$_2$;
$R^{5'}$ is H, —OH, —O—R$^6$, —OSO$_3$M, —OPO$_3$M$_2$, —CH$_2$OH, —CH$_2$OSO$_3$M, or —CH$_2$OPO$_3$M$_2$;
M is hydrogen or a counterion;
$R^{6'}$ is a branched or unbranched alkyl;
X is —N(H)—, —C(O)N(H)—, —C(O)N(R$^{7'}$)—, —N(R$^{7'}$)—, or —O—;
$R^{7'}$ is a branched or unbranched alkyl or a cycloalkyl;
Y is —O—, —N(H)—, or —N(R$^{8'}$)—;
$R^{8'}$ is a branched or unbranched alkyl or a cycloalkyl;
Z is O or H$_2$;

⋰⋰ represents a single or double carbon-carbon bond between C4 and C5 or C5 and C6;

⋰⋰⋰ represents a single, double, or a triple carbon-carbon bond between C22 and C23;

∫ at C3, C5, C7, C12, C20, and C24 represents a bond to the attached substituent that is either in front of (β) or behind (α) the plane of the paper, and defines the R or S absolute configuration of the carbon atom that bears the attached substituent;
m is 1, 2, 3, or 4;
n is 1, 2, 3, or 4;
k is 0, 1, or 2;
p is 0, 1, or 2;
q is 0 or 1; and
r is 0, 1, 2, or 3;
with the proviso that R$^{1'}$ is not 2-(N-pyrrolidino)ethylamino.

In the compounds of Formula II, the organic groups (e.g., alkyls, alkenyls, cycloalkyls, aryls, heteroaryls) are of a size that does not disrupt the function of the compound.

In certain preferred embodiments of Formula II, $R^{2'}$ and $R^{3'}$ are independently selected from the group consisting of H, —OH, —OSO$_3$M, and —OPO$_3$M$_2$. In certain more preferred embodiments of Formula II, $R^{2'}$ and $R^{3'}$ are independently selected from the group consisting of H, —OH, and —OSO$_3$M. In certain even more preferred embodiments of Formula II, at least one of $R^{2'}$ and $R^{3'}$ is —OH or —OSO$_3$M.

In certain preferred embodiments of Formula II, $R^{4'}$ is H, a branched or unbranched alkyl, a branched or unbranched alkenyl (having one or more carbon-carbon double bond), a cycloalkyl, an aryl, a heteroaryl, —(CH$_2$)$_r$OH, —(CH$_2$)$_r$OSO$_3$M, or —(CH$_2$)$_r$OPO$_3$M$_2$. In certain more preferred embodiments of Formula II, $R^{4'}$ is H, a branched or unbranched alkyl having six carbons or less, an alkenyl having six carbons or less, an aryl having six carbons or less, or a heteroaryl having five carbons or less, —(CH$_2$)$_r$OH, or —(CH$_2$)$_r$OSO$_3$M.

In certain more preferred embodiments of Formula II, $R^{4'}$ is H, an alkyl having six carbons or less, a heteroaryl having five carbons or less, —(CH$_2$)$_r$OH, or —(CH$_2$)$_r$OSO$_3$M. In certain even more preferred embodiments of Formula II, $R^{4'}$ is H, an alkyl having six carbons or less, —(CH$_2$)$_r$OH, or —(CH$_2$)$_r$OSO$_3$M. In certain even more preferred embodiments of Formula II, $R^{4'}$ is H or an alkyl having six carbons or less.

In certain preferred embodiments of Formula II, $R^{5'}$ is H, —OH, —O—R$^{6'}$, —OSO$_3$M, —OPO$_3$M$_2$, —CH$_2$OH, —CH$_2$OSO$_3$M, or —CH$_2$OPO$_3$M$_2$. In certain more preferred embodiments of Formula II, $R^{5'}$ is —OH, —OSO$_3$M, —CH$_2$OH, or —CH$_2$OSO$_3$M.

In certain preferred embodiments of Formula II, M is H or a counterion, and more particularly, H, Na, K, Ca, NH$_4$, or R$_4$N, wherein each R is independently a branched or unbranched alkyl (preferably, unbranched) having four carbons or less. In certain more preferred embodiments of Formula II, M is a Na, K, or NH$_4$ counterion. In certain even more preferred embodiments of Formula II, M is a Na counterion.

In certain preferred embodiments of Formula II, $R^{6'}$ is a branched or unbranched alkyl having six carbons or less.

In certain preferred embodiments of Formula II, X is —N(H)— or —C(O)N(H)—. In certain more preferred embodiments of Formula II, X is —N(H)—.

In certain preferred embodiments of Formula II, $R^{7'}$ is a branched or unbranched alkyl or cycloalkyl having six carbons or less.

In certain preferred embodiments of Formula II, $R^{8'}$ is a branched or unbranched alkyl or cycloalkyl having six carbons or less.

In certain preferred embodiments of Formula II, Z is O.

In certain preferred embodiments of Formula II, m is 1, 2, or 3. In certain more preferred embodiments of Formula II, m is 1 or 2.

In certain preferred embodiments of Formula II, n is 1, 2, or 3. In certain more preferred embodiments of Formula II, n is 2 or 3.

In certain preferred embodiments of Formula II, k is 0 or 1. In certain more preferred embodiments of Formula II, k is 0.

In certain preferred embodiments of Formula II, p is 0 or 1. In certain more preferred embodiments of Formula II, p is 0.

In certain preferred embodiments of Formula II, q is 0.

In certain preferred embodiments of Formula II, r is 0, 1, or 2.

In certain preferred embodiments of Formula II, q is 0 or 1; p is 0 or 1; n is 1, 2, or 3; m is 1, 2, or 3; k is 0 or 1; X is —N(H)— or —C(O)N(H)—; Z is O or H$_2$; $R^{2'}$ and $R^{3'}$ are independently selected from the group consisting of H, —OH, and —OSO$_3$M; $R^{4'}$ is H, an alkyl having six carbons or less, a heteroaryl having five carbons or less, —(CH$_2$)$_r$OH, or —(CH$_2$)$_r$OSO$_3$M, wherein r is 0, 1, or 2; $R^{5'}$ is —OH, —OSO$_3$M, —CH$_2$OH, or —CH$_2$OSO$_3$M; and M is a Na, K, or NH$_4$ counterion.

In certain preferred embodiments of Formula II, q is 0; p is 0 or 1; n is 2 or 3; k is 0; X is —N(H)— or —C(O)N(H)—; Z is O; $R^{2'}$ and $R^{3'}$ are independently selected from the group consisting of H, —OH, and —OSO$_3$M; $R^{4'}$ is H, an alkyl having six carbons or less, —(CH$_2$)$_r$OH, or —(CH$_2$)$_r$OSO$_3$M wherein r is 0, 1, or 2; $R^{5'}$ is —OH, —OSO$_3$M, —CH$_2$OH, or —CH$_2$OSO$_3$M; and M is a Na counterion.

In certain preferred embodiments of Formula II, q is 0 or 1; p is 0 or 1; n is 2 or 3; m is 1 or 2; k is 0 or 1; X is —N(H)— or —C(O)N(H)—; Z is O or $H_2$; at least one of $R^{2'}$ and $R^{3'}$ is —OH or —$OSO_3M$; $R^{4'}$ is H or an alkyl having six carbons or less; $R^{5'}$ is —OH, —$OSO_3M$, —$CH_2OH$, or —$CH_2OSO_3M$; and M is a Na counterion.

In certain preferred embodiments of Formula II, q is 0; p is 0; n is 2 or 3; k is 0; X is —N(H)—; Z is O; at least one of $R^{2'}$ and $R^{3'}$ is —OH or —$OSO_3M$; $R^{4'}$ is H or an alkyl having six carbons or less; $R^{5'}$ is —OH, —$OSO_3M$, —$CH_2OH$, or —$CH_2OSO_3M$; and M is a Na counterion.

In certain preferred embodiments of Formula II, $R^1$ is not 2-(N-pyrrolidono ethylamino.

A particularly preferred compound of Formula II is petromyzonamine disulfate (3), which has the following structure:

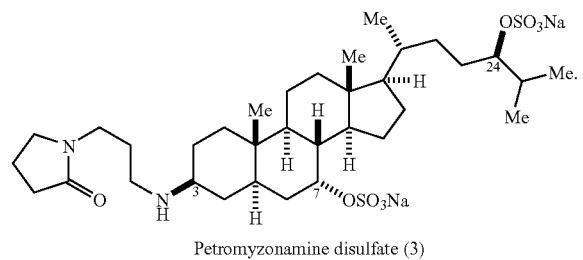

Petromyzonamine disulfate (3)

Compounds of Formulae I and II can be used alone or in combination. They can also be used in combination with, for example, petromyzonol sulfate (1) (shown below) or other compounds such as allocholic acid, 3-ketoallocholic acid, 3-ketopetromyzonol, 3-ketopetromyzonol sulfate, arginine, or other common bile acids or derivatives thereof, such as those produced by sea lamprey.

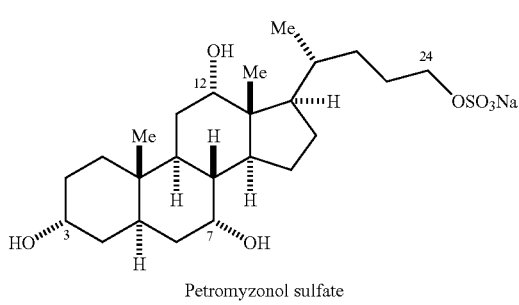

Petromyzonol sulfate

Thus, the present invention provides lamprey attractant compositions that include one or more compounds of Formula I and/or Formula II, optionally with other compounds. The compounds of Formula I and/or Formula II are preferably present in an amount of at least 1 wt-% (more preferably, at least 10 wt-%).

In certain compositions of the present invention, there is provided a lamprey attractant composition that includes at least $10^{-5}$ Molar (M) of an attractant, wherein the attractant is a compound of Formula I, a compound of Formula II, or a combination of compounds of Formula I and Formula II. Other compounds can also be present in such compositions.

Certain specific compounds of Formulae I and II can be isolated from sea lamprey larval holding water, for example. This can be done using an extensive regimen of isolation and purification, which is described in detail in the Examples Section. This could involve using waters from streams that contain these organisms or culturing larval lamprey in the laboratory. Larval lamprey can be held in tanks at densities of at least 1 animal (typically, 1-5 animals) per liter where they may be fed yeast (Polkinghorne et al., Fish Physiology and Biochemistry, 24:15-30 (2001)). Extracts from both these sources, or from streams or other waters, could then be concentrated by passage through extraction resins, such as XAD7HP or XAD2000 porous polymeric adsorbents (available from Rohm and Haas, Philadelphia, Pa.), or reverse phase silica gel resins, or the like, which can be held in columns of various sizes, and eluted with methanol or other organic solvents which may then be concentrated by rotary-evaporation or by other means.

These compounds might also be extracted from laboratory cultures of lamprey liver cells, which can be maintained under standard laboratory in vitro cell culture conditions and used a source for these compounds (Collodi, Progress Report Great Lakes Fishery Commission (2000)). They would be extracted in the same manner as larval culture waters.

Figure 2A:
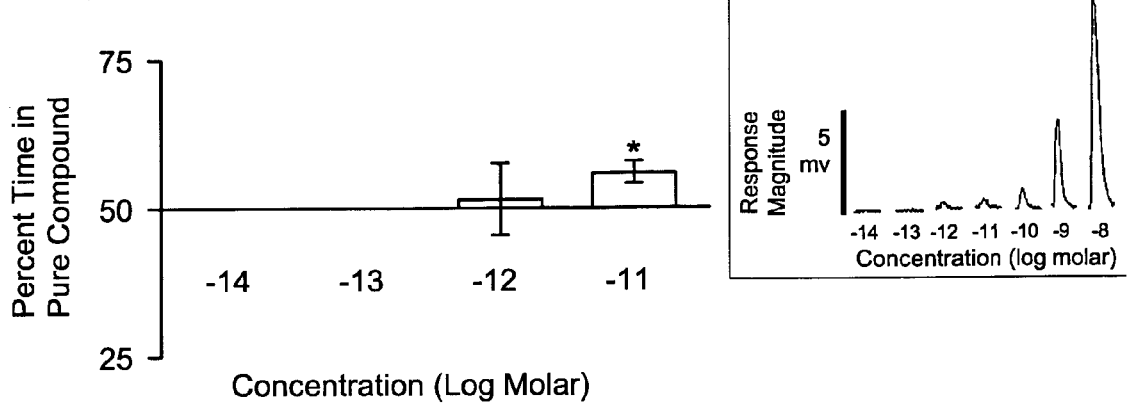
FIG. 2. Biological activity of the three pheromones. Mean percent time (±95% confidence intervals) spent by adult sea lampreys in: (a) petromyzonol sulfate; (b) petromyzosterol disulfate; and (c) and petromyzonamine disulfate in the behavior maze (N=14 trials of 4 lampreys for each experiment). Means were compared to a no-preference value of 50% using a student's T-test; *p<0.05. Insets for each compound show representative dose-responses using EOG recording for each compound ranging from $10^{-14}$ M to $10^{-8}$ M.
Figure 2B:
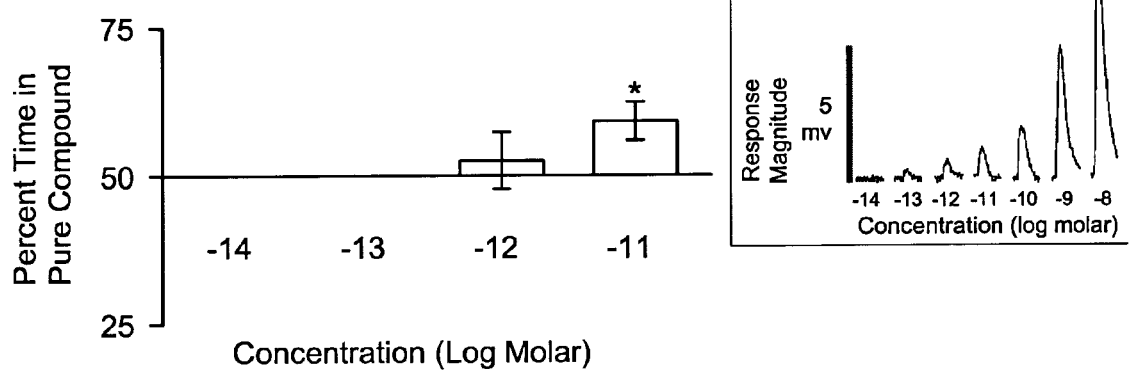
Figure 2C:
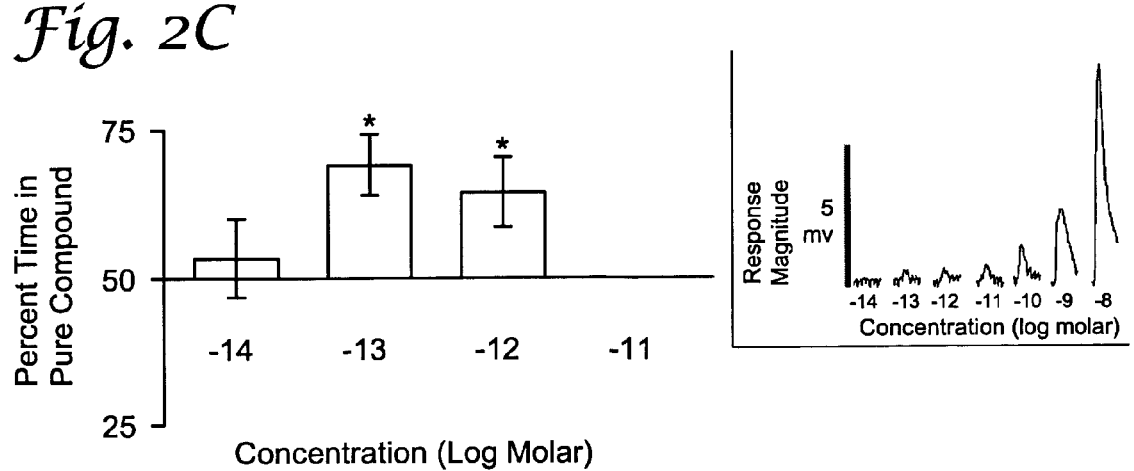

Three compounds and a variety of related products can be isolated in this way. Typically, one of the least abundant compounds with olfactory and behavioral activity in sea lamprey is petromyzonol sulfate (1). It displays only weak and somewhat inconsistent behavioral activity even at $10^{-11}$ M (FIG. 2a). The second most abundant component is attractive at $10^{-11}$ M while EOG recording found it to be detected down to $10^{-12}$ M (FIG. 2b). Various experiments indicated this compound has at least two protic (OH— or NH— containing) functional groups, at least one sulphate group (ROSO3—), a mass of 590 amu, and has the structure shown in FIG. 3 (petromyzosterol disulfate (2)). The third component appears to be the most important as it can strongly attract sea lamprey at both $10^{-13}$ and $10^{-12}$ M and stimulated EOG responses at concentrations ranging down to $10^{-13}$ M (FIG. 2c). Various experiments indicated that this compound has two protic groups, two sulphate groups, a mass of 703.3635, and has the structure shown in FIG. 3 (petromyzonamine disulfate (3)).

The syntheses of specific compounds 2 and 3 as well as of compounds of general Formulae I and II are described as follows: Scheme 1 outlines the synthesis of (petromyzosterol disulfate (2); Scheme 2 outlines the syntheses of compounds of Formula I; Scheme 3 outlines the syntheses of ylide reagents used in Scheme 2; Scheme 4 outlines the synthesis of (petromyzonamine disulfate (3); Scheme 5 outlines the syntheses of ketone intermediates used in syntheses of compounds of Formula II; Scheme 6 outlines the final stages of syntheses of compounds of Formula II; Scheme 7 outlines the synthesis of a specific compound of Formula I; Scheme 8 outlines the synthesis of ylide reagent used in Scheme 7; Scheme 9 outlines the synthesis of the ketone intermediate used in a synthesis of a specific compound of Formula II; Scheme 10 outlines the final stage of synthesis of a specific compound of Formula II. In the schemes and the discussions that follow, the structures are numbered in sequence within each Scheme according to the convention of #.$, where # is the Scheme number and $ is the compound number within that Scheme. For example, compound 3.4 is the fourth compound in Scheme 3.

Petromyzosterol disulfate (2) can be made using the following method (Scheme 1). Deoxycholic acid (1.1) is acetylated with acetyl chloride/pyridine, for example, to provide 3,7-diacetyldeoxycholic acid (1.2), which is cleaved under oxidative conditions with lead tetraacetate/cupric chloride, for example, to yield primary olefin 1.3 (Tochtrop et al., Bioorg. Med. Chem. Lett., 12, 433-436 (2002)). Ozonolysis further cleaves the side chain to aldehyde 1.4. This is reacted with an ylide (step d) in a Wittig reaction to furnish compound 1.5, which has the carbon skeleton present in 2. Preparation of the ylide reagent is described in Scheme 3.

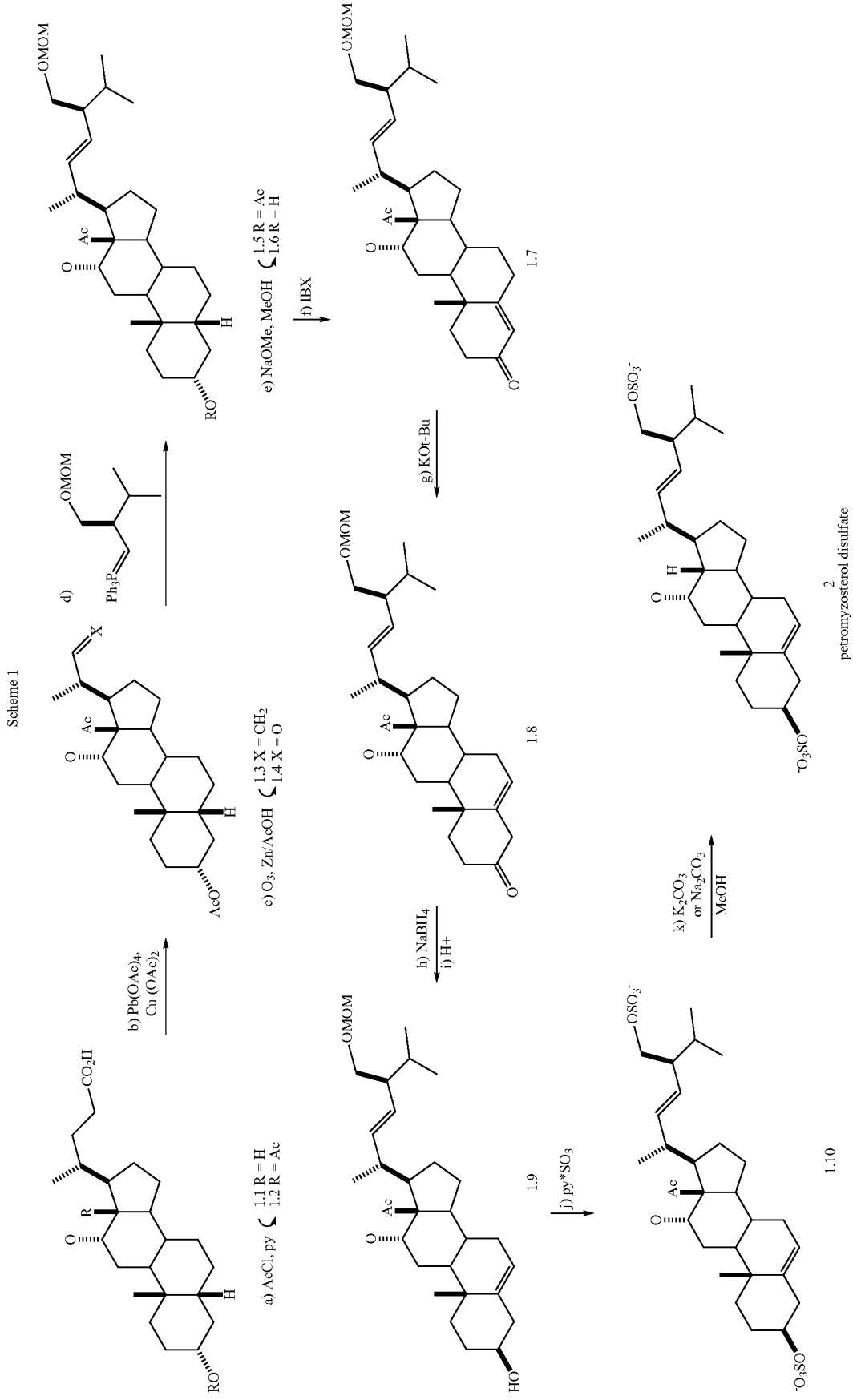

Selective removal of acetyl group at position C3 in 1.5 with a base (NaOMe, K$_2$CO$_3$, etc.) results in 1.6 (Gao et. al., *Synth. Comm*, 27, 757-776 (1997)). Oxidation with 2.5 equivalents IBX (iodoxylbenzoic acid), for example, gives enone 1.7 (Zhang et. al., *Org. Lett.* 5, 3257-3260 (2003) and Nicolaou et al., *J. Amer. Chem. Soc.* 124, 2245-2258 (2002)).

Deconjugation with an alcoholate base like potassium tert-butoxide gives ketone 1.8. (Nilsson et al., *J. Med. Chem.*, 41, 2604-2613 (1998)). Stereoselective reduction with sodium borohydride, for example, followed by acid catalyzed deprotection of the methoxymethyl ether (OMOM) delivers 1.9. Sulfation of both 3-OH and 24$^1$-OH with the pyridine•sulfur trioxide complex (py.SO$_3$) results in disulfate 1.10 having pyridinium cations. Final deprotection of the 12-acetyl group under basic conditions liberates the 12-OH and replaces the counterions like K$^+$ or Na$^+$.

Compounds of Formula I can be made using the following general method (Schemes 2 and 3). These syntheses can begin with any of cholic, chenodeoxycholic, deoxycholic, or lithocholic acid (2.1). Protection (step a) acetylates all carbinol hydroxyl groups with acetic anhydride/pyridine to give 2.2. Oxidative cleavage of the side chain with lead tetraacetate/cupric chloride, for example, gives 2.3, which is further cleaved in the ozonolysis reaction to yield 2.4. Wittig reaction with two types of phosphorus ylides (see Scheme 3) and further elaboration of the side chain furnishes 2.5.

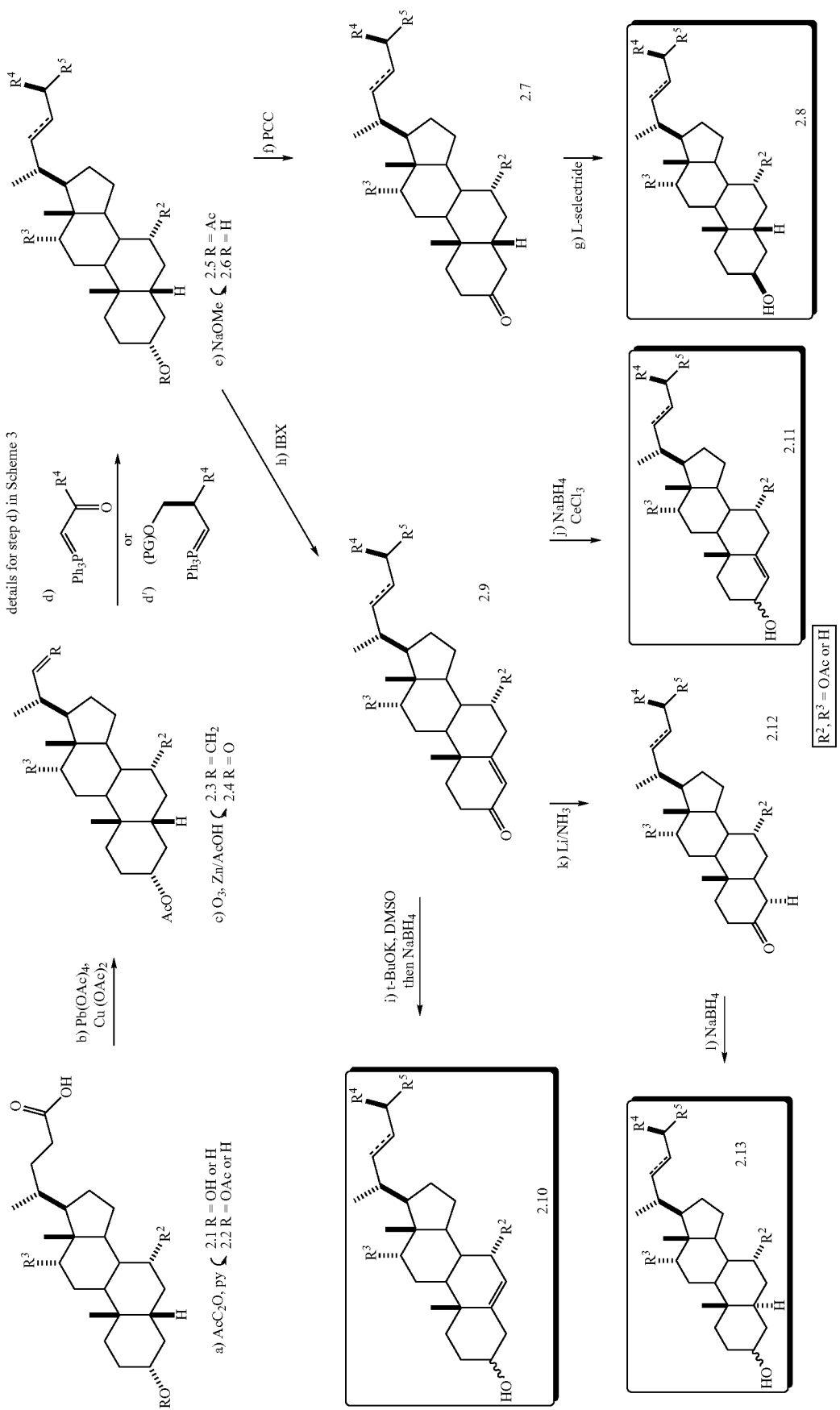

Common intermediate 2.5 is selectively deacetylated at O-3 and the resulting 2.6 is diversified to provide various structures represented in Formula I. For example, PCC oxidation (structure 2.7) followed by reduction with L-Selectride inverts the orientation of 3-OH from α to β to provide compound 2.8.

In another variation, 2.6 is converted to the enone 2.9 by means of IBX oxidation, for example. Deconjugation with potassium tert-butoxide followed by the reduction with sodium borohydride conveniently results in sterol 2.10.

In yet another variation, enone 2.9 can be treated with a mixture of sodium borohydride and cerium (III) chloride to selectively reduce the carbonyl group, and not the conjugated double bond, to furnish the allylic alcohol 2.11.

In a further variation, enone 2.9 can be reduced to the saturated ketone 2.12 with lithium metal in liquid ammonia (Shu et al., *Steroids I*, 67, 291-304 (2002)). This method of reduction gives the trans (5α) junction between rings A and B. The trans saturated ketone 2.12 is reduced with sodium borohydride (or other reducing agents) to give the 3α-OH or 3β-OH steroid 2.13.

The method outlined in Scheme 2 allows the incorporation of a large variety of the side chain structures where the source of $R^4$ is an acyl chloride 3.1. As shown in Scheme 3, 3.1 is converted into the Weinreb amide 3.2, which acylates a carbanion generated from diethyl methylphosphonate and n-butyllithium to provide the phosphonate 3.3. Horner-Wadsworth-Emmons reaction with the aldehyde 2.4 gives enones 3.4, which can either be reduced with a mixture of sodium borohydride and cerium (III) chloride to give the allylic alcohols 3.5 or hydrogenated to ketones 3.6, which upon treatment with sodium borohydride yield a saturated alcohol 3.7.

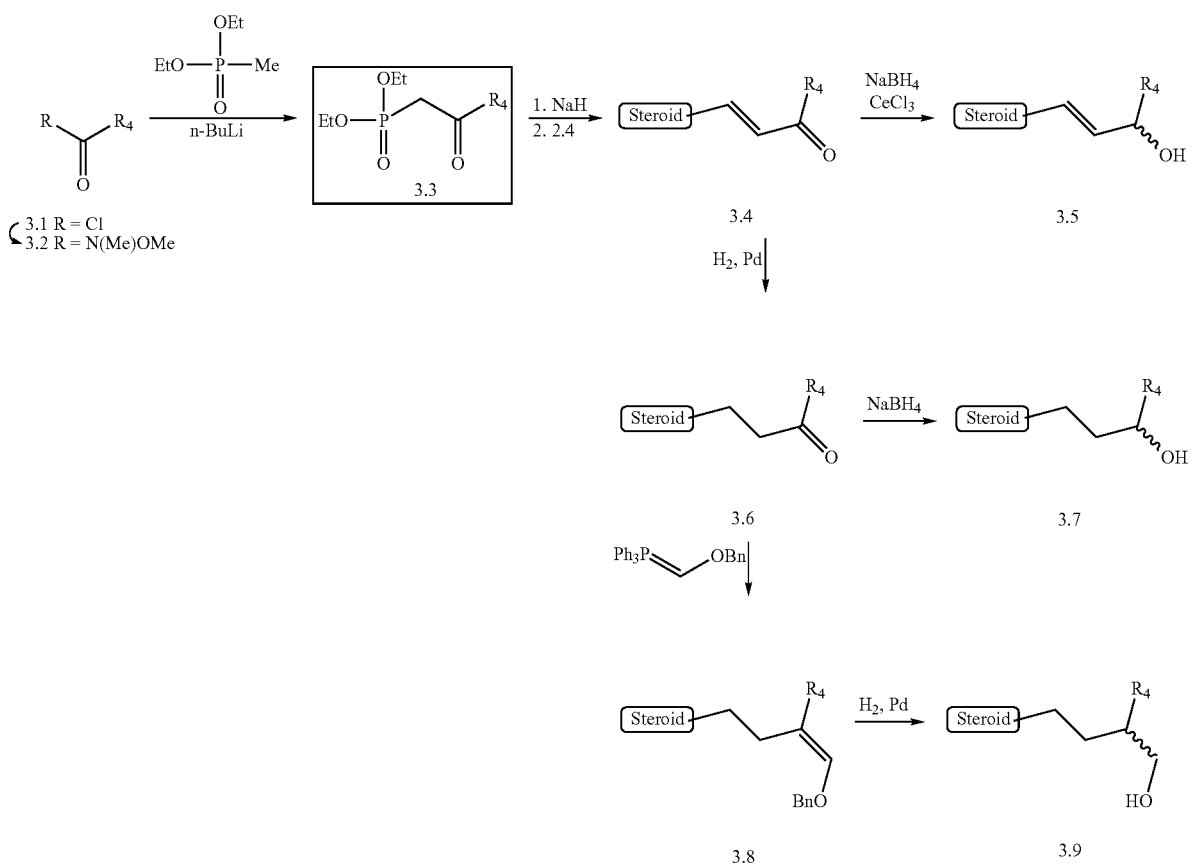

Scheme 3

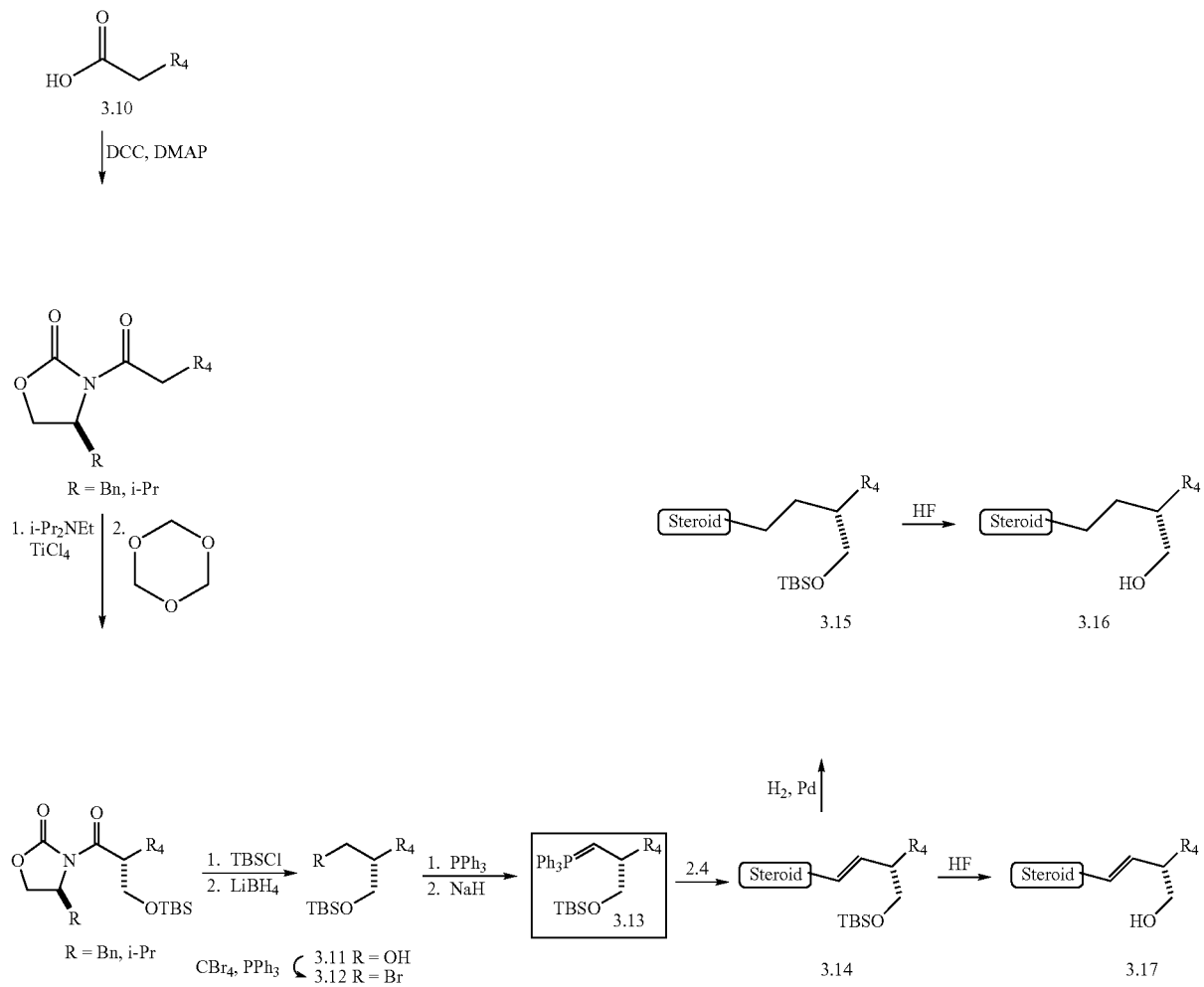

To generate a variety of $R^5$ groups to the ketone 3.6 is reacted with an ylide like benzyloxymethylidene triphenylphosphorane to furnish olefins 3.8, which are saturated and deprotected in a single step by hydrogenation to provide 3.9.

To create structures with a side chain like that of natural product 2, an alternative approach may be employed. It begins with a carboxylic acid of a general structure 3.10. Evans aldol methodology (Watson et al., *Tet. Lett.*, 43, 683-686 (2002)) general article) allows synthesis of primary alcohols 3.11, which are converted to bromides 3.12. These, in turn, are used to prepare the ylide reagents 3.13. Wittig reaction between aldehyde 2.4 and 3.13 gives olefin 3.14. Hydrogenation saturates the double bond to give 3.15. Removal of the TBS protecting group with aqueous HF, for example, yields 3.16 and desilylation of 3.14 gives 3.17.

Various hydroxyl group sulfation or phosphorylation reactions and hydroxyl group deprotection steps at multiple points in the synthesis are used to install various numbers and locations of sulfate and phosphate groups present in Formula I compounds.

Petromyzonamine disulfate (3) can be made using the following method (Scheme 4; Steps b) through e) are described in Zhang et al., *Org. Lett.*, 5, 3257-3259 (2003)). Chenodeoxycholic acid (4.1) is converted into its methyl ester 4.2 under Fischer esterification conditions: methanol and a catalytic amount of the strong acid like HCl. Selective oxidation of the equatorial 3-α-OH with silver carbonate on celite gives ketone 4.3 (Joyce et al., *Steroids*, 44, 95-102 (1984)). The 7-α-OH is protected as the MOM ether in compound 4.4. IBX dehydrogenation produces enone 4.5. Lithium/ammonia reduction yields ketone-aldehyde 4.6. Regioselective introduction of the isopropyl group relies on the higher reactivity of an aldehyde carbonyl groups vs. that of a ketone. Addition of diisopropylzinc or isopropylmagesium bromide produces carbinols 4.8 epimeric at C24, which can be derivatized and separated by means of chromatography. Otherwise use of a chiral ligand like 4.7 helps selectively produces the C24-β-epimer 4.8.

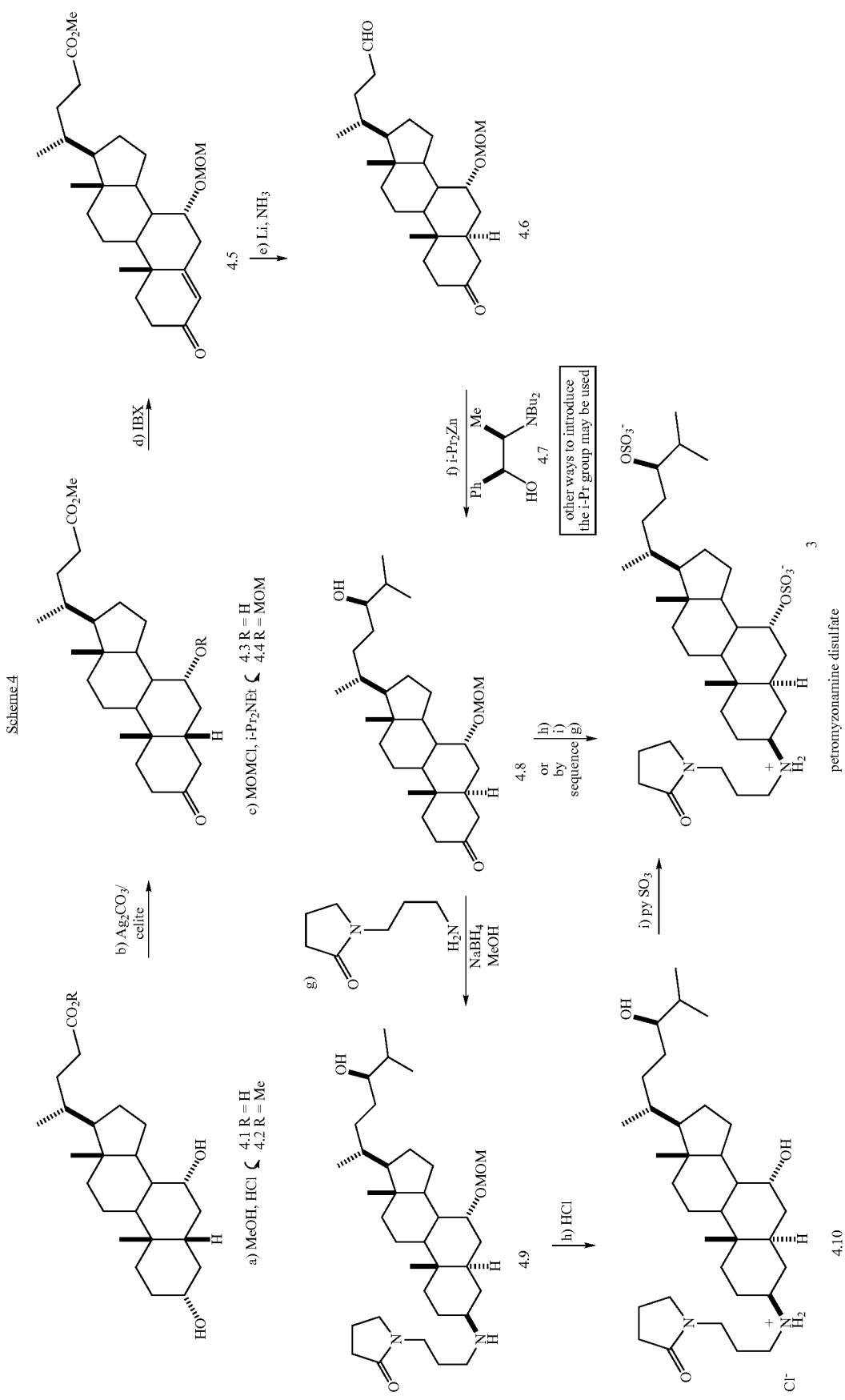

Reductive amination of ketone 4.8 with 3-aminopropylpyrrolidinone and sodium borohydride in methanol results in 4.9. When done at −78° C. the reaction generates predominantly the 3-β-epimer. Removal of the MOM group under acidic conditions and sulfation of both alcohols completes the synthesis of 3. This can also be achieved by the alternative sequence of deprotection (h), sulfation or (i), and amination (g).

Compounds of Formula II can be made using the following general method (Schemes 5 and 6). These syntheses begin with any of cholic, chenodeoxycholic, deoxycholic, or lithocholic acid (5.1). Esterification gives 5.2. Selective oxidation of the 3-OH with silver carbonate on celite gives ketones 5.3. Protection of the remaining hydroxyl groups as MOM ethers gives 5.4. These intermediates are points of departure for synthesizing many compounds of Formula II. In one route, protection of the ketone as the ethylene ketal followed by DIBAL reduction gives aldehyde 5.5. Reaction with a suitable organometallic reagent and removal of MOM groups yields ketones 5.6. In another route, ketones 5.4 are dehydrogenated to the enones 5.7 by means of IBX. These enones can either be reduced with lithium/ammonia conditions to give the aldehyde-ketones 5.8, which upon regioselective addition of an organometallic reagent give 5-α configured ketones 5.9. Or, the enone 5.7 can be ketalized with ethylene glycol to give compounds 5.10, wherein the double bond has migrated from Δ-4 to Δ-5. DIBAL reduction furnishes aldehydes 5.11. Similar addition of an organometallic reagent results in the incorporation of the desired $R^4$ group. Removal of the ketal protecting group depending on the conditions furnishes 5.12 or 5.13. Ketones 5.6, 5.9, 5.12, and 5.13 are used as described in Scheme 6 to furnish the final products.

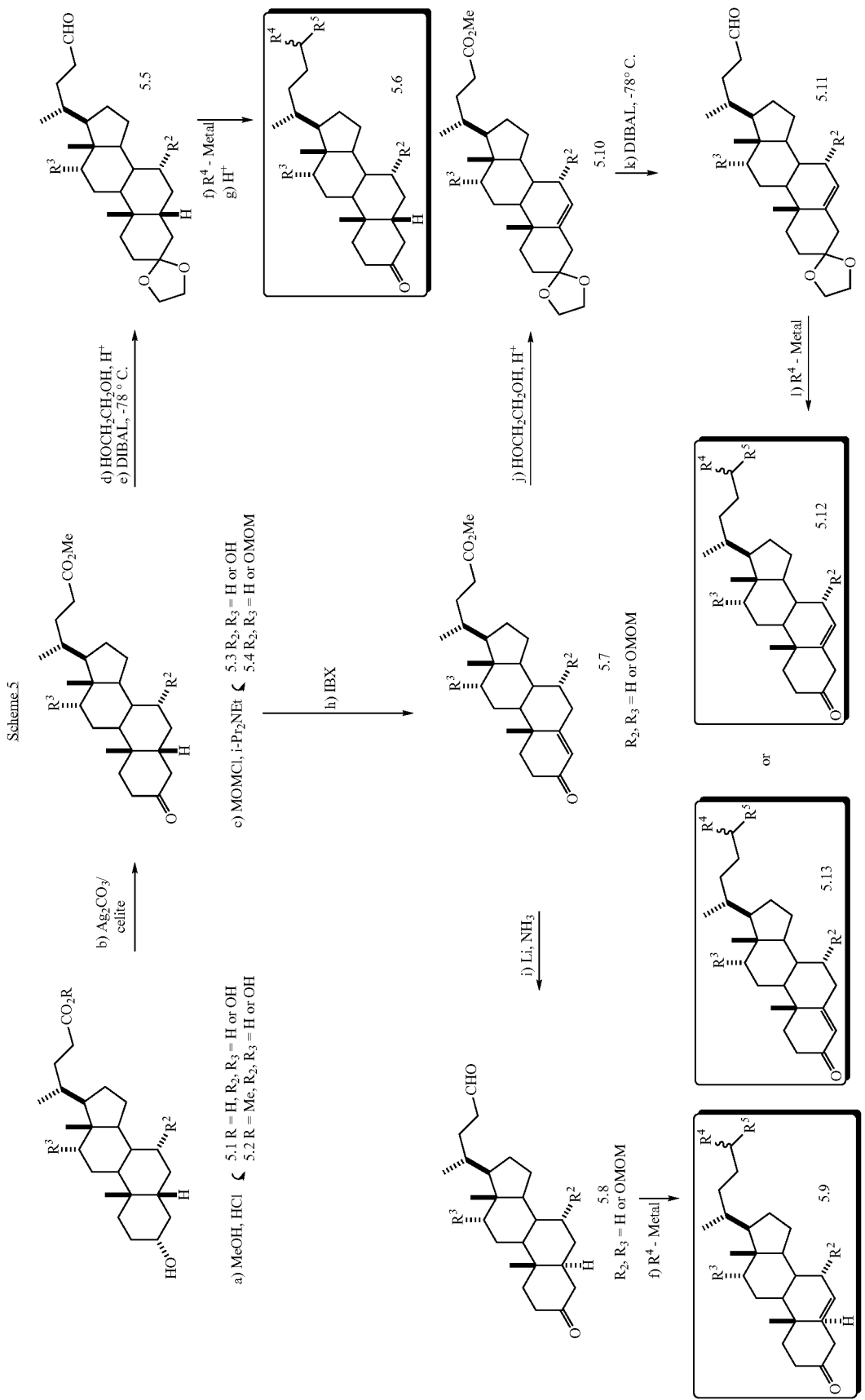

The final stages of the syntheses involve reductive amination of 6.1 with $R^1NH_2$ to give 6.2. For example, the removal of the MOM protection produces 6.4, sulfation or phosphorylation provides 6.5. The sequence of MOM deprotection, sulfation or phosphorylation, and reductive amination steps may be reversed as described in Scheme 4.

Scheme 6

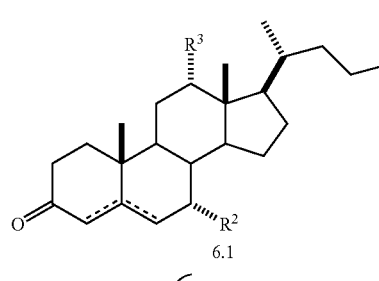

6.1 a) py $OSO_3$ ⟶ $R^2, R^3$ = H or OMOM
$R^5$ = OH 6.2
$R^2, R^3$ = H or OMOM
$R^5 = OSO_3^-PyH^+$ b) $H_2N-R^1$ / $NaBH_4$ / MeOH

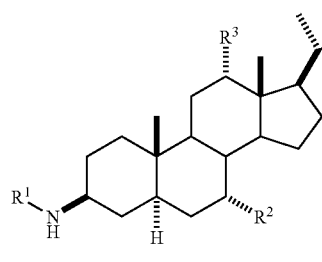

c) HCl 6.3
$R^2, R^3$ = H or OMOM
$R^5 = OSO_3^-PyH^+$ $R^4$ = Alk, Alkenyl, CycloAlk, Ar.

-continued

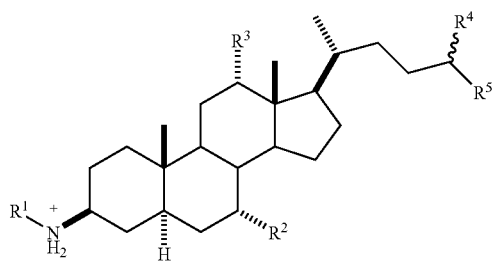

6.4
$R^2, R^3$ = H or OH
$R^5 = OSO_3^-$ d) py $SO_3$

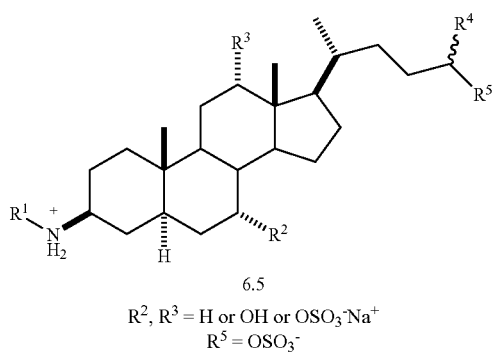

6.5
$R^2, R^3$ = H or OH or $OSO_3^-Na^+$
$R^5 = OSO_3^-$

As exemplary synthesis of a specific compound of Formula I is outlined in Schemes 7 and 8. Chenodeoxycholic acid (7.1) is converted into diacetate 7.2, which is oxidatively cleaved to 7.3. Ozonolysis of 7.3 yields 7.4, which is reacted with the ylide 7.5 (see Scheme 8). The resulting 7.6 is regioselectively deacetylated to form 7.7, which is oxidized with IBX to 7.8. The enone 7.8 is reduced with lithium/ammonia to 7.9. Sodium hydroxide and fluoride cleave both the TBS and acetate protecting groups and the resulting carbinols are sulfated with py.$SO_3$. Finally, the 3-ketone is reduced to 7.10 with sodium borohydride.

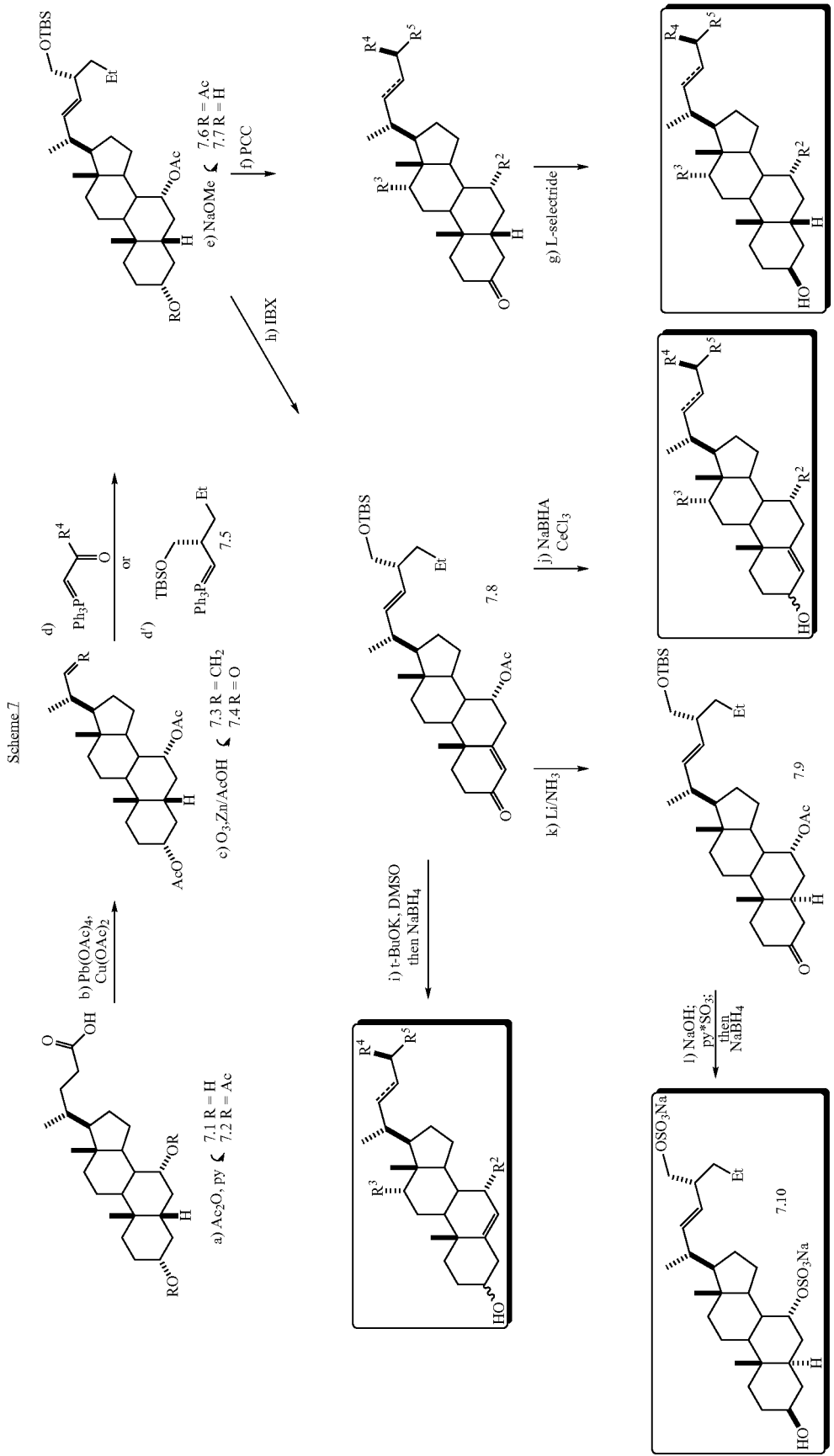

Butyric acid 8.1 is converted to the alcohol 8.2 via the well-known Evans aldol methodology. Bromide 8.3 is obtained in reaction of 8.2 with carbon tetrabromide and triphenylphosphine. Bromide 8.3 produces the ylide reagent 8.4 by deprotonation of the intermediate phosphonium salt and 8.4 is coupled with 7.4.

Scheme 8

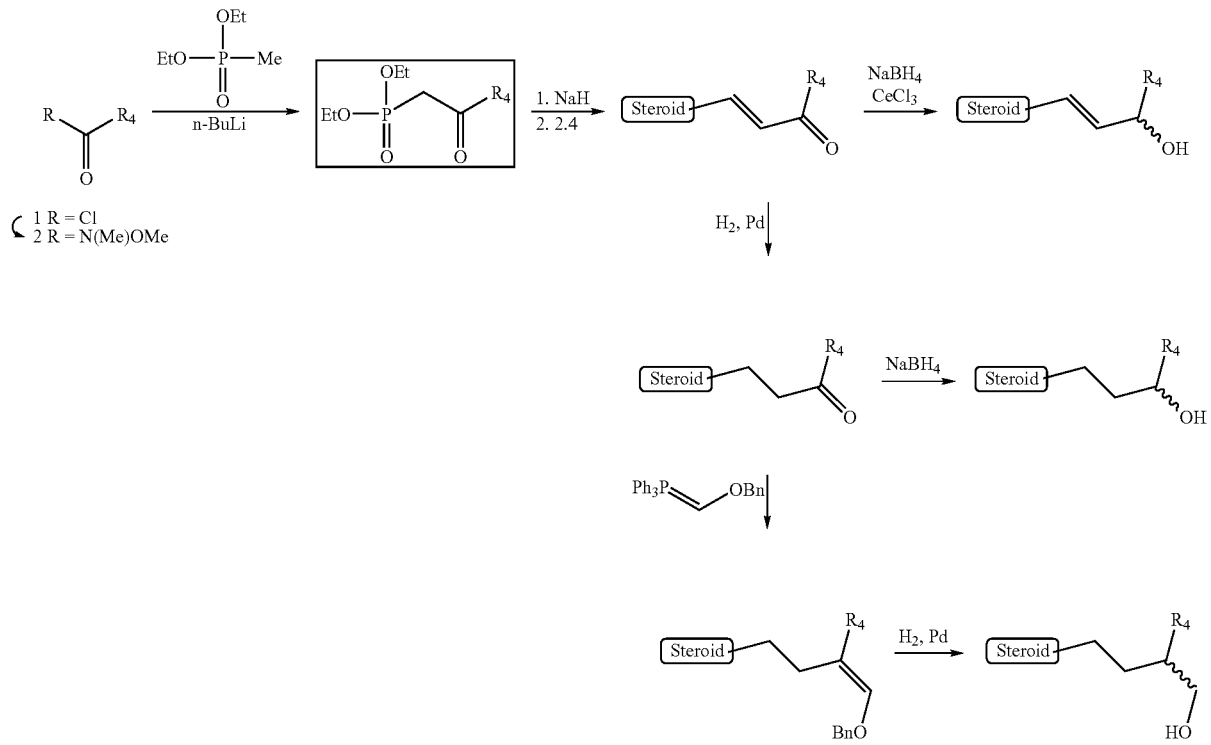

Stereoselective Synthesis of C-24 epimer

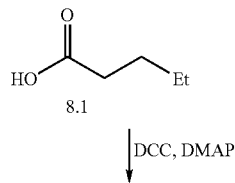

8.1

DCC, DMAP

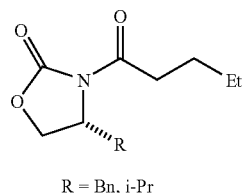

R = Bn, i-Pr 1. i-Pr$_2$NEt
   TiCl$_4$
2. 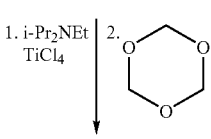

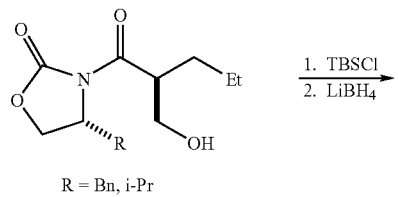

R = Bn, i-Pr

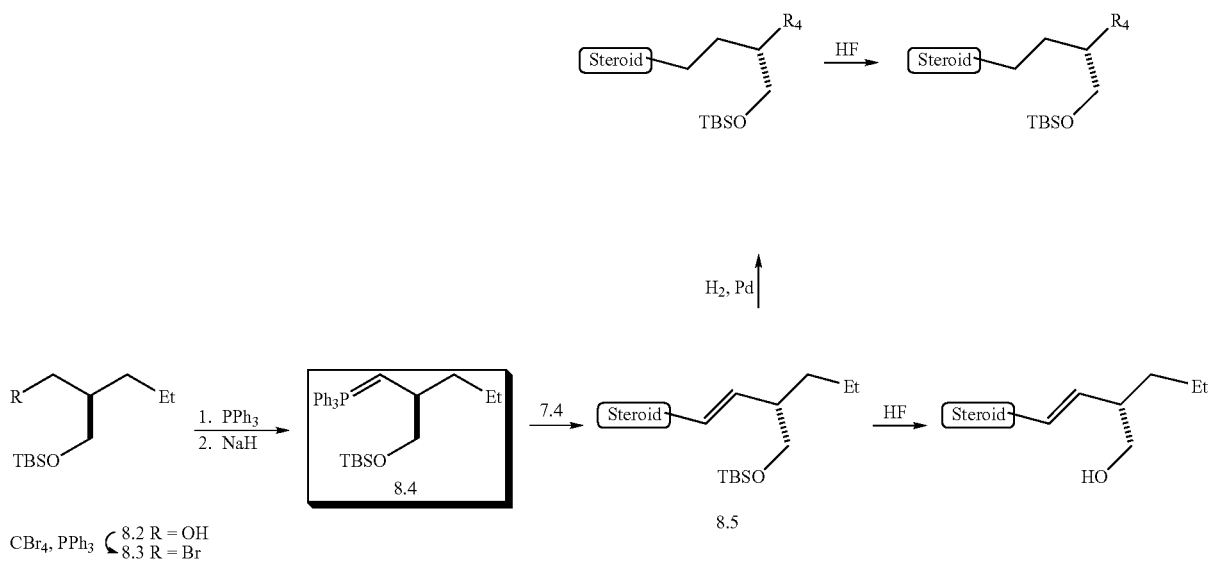

A method for preparing a specific compound of Formula II is described in Schemes 9 and 10. Deoxycholic acid (9.1) is converted into its methyl ester 9.2, which is oxidized to ketone 9.3. The carbinol OH in 9.3 is protected as its MOM ether to yield 9.4. IBX dehydrogenation yields 9.5, which is reduced with lithium/ammonia to furnish 9.6. The more reactive aldehyde group in 9.6 reacts with 1 equivalent of the Grignard reagent to give 9.7.

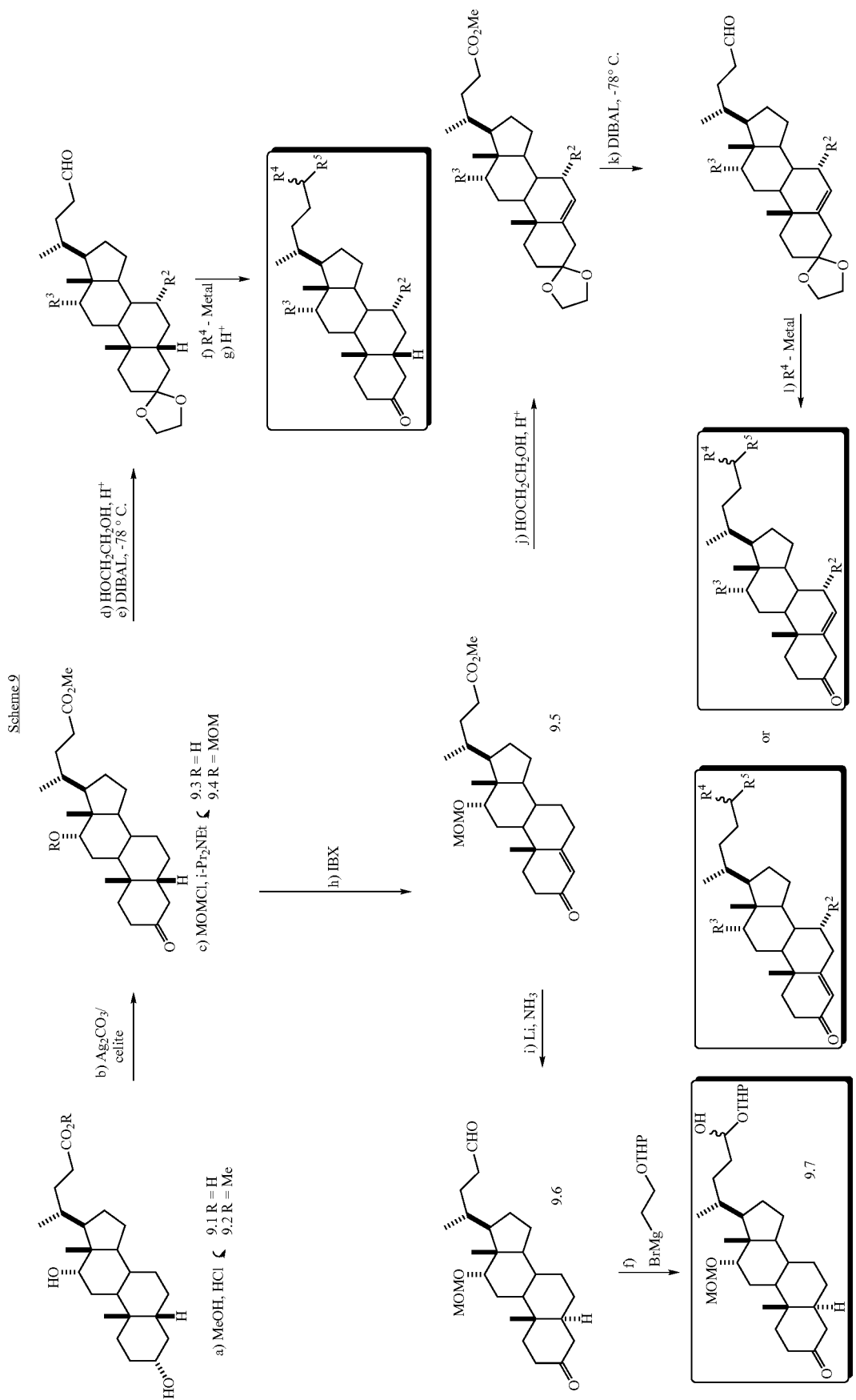

Ketone 10.1 (which is also 9.7) is sulfated on its free carbinol to yield 10.2. Reductive amination provides 10.3, which is treated with hydrochloric acid to remove MOM and THP protecting groups and produce the final compound 10.4, which is an apprixmate 1:1 mixture of epimers at C24.

Lakes Res., 29 (Supplement 1): 66-84 (2003); Twohey et al., J Great Lakes Res 29 (Supplement 1): 794-800 (2003)).

Compounds of the present invention might also be added to traps at various locations so that the collected animals could be put to a use, i.e., as a food source, for use in research and

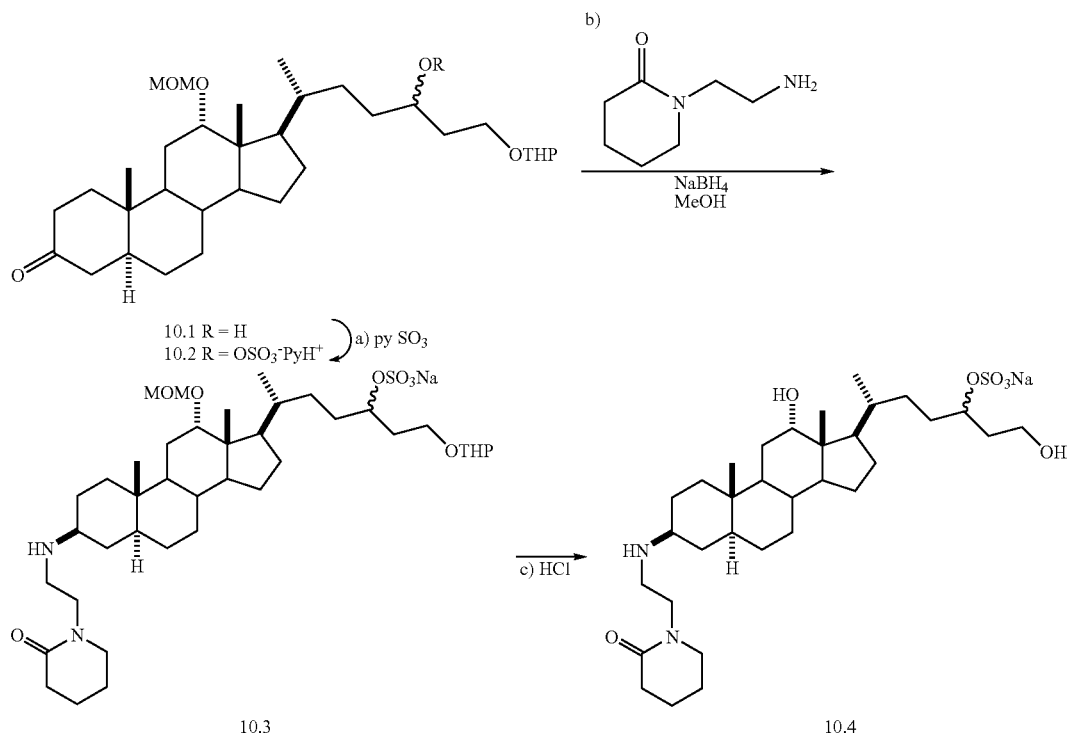

Compounds of the present invention can be used to control populations of lamprey, particularly sea lamprey, whether they be adult or larval lamprey. At least four options appear to exist. First, the compounds of the present invention can be used to attract lamprey to sites equipped with traps or nets for collection or that can easily be treated with toxins. These sites might either be tributaries of rivers, rivers, lakes, marine estuaries, ponds, creeks, or perhaps the ocean. Collected migratory animals might then be sterilized and released for population control, or removed and destroyed, either for simple removal and/or population assessment. Second, the compounds might be added to barrier sites which block lamprey movement to attract them and prevent them from straying to other locations because their movement upstream is blocked. Third, the compound(s) could be added at high concentrations or in unnatural mixtures or ratios to particular locations to promote behavioral confusion or perhaps repulsion, thereby disrupting upstream movement (a strategy commonly known as 'pheromonal disruption' in insect control), and/or disrupting reproductive success, or to otherwise disrupt lamprey behavior. Fourth, the compound(s) might be added to locations that can not support lamprey spawning or that support lamprey but are not easily treated by other means and to which lamprey do not normally travel, thereby diverting them from their usual migratory patterns into areas that can not support spawning and/or larval survival and reducing overall reproductive success (Sorensen and Vrieze, J Great teaching, or exporting lamprey for use elsewhere such restocking for conservation. They could also be put in barriers.

Compounds of the present invention might be added to streams that presently do not support lamprey spawning to re-establish lamprey runs for the purposes of conservation.

In addition to being useful in control and management of migrating adult sea lamprey, it is likely that petromyzonol sulfate (1) and compounds of the present invention can be used as larval sea lamprey attractants, and thus could be used in traps to remove larvae as well. It has been speculated that larval sea lamprey odor (pheromones) stimulates sexual maturation of adults by acting as a priming pheromone; these compounds might be employed to stimulate or accelerate adult maturation in streams or in aquaculture systems.

Compounds of the present invention could be employed with additional sensory cues such as light, water flow, and other chemical attractants such as the sea lamprey sex pheromone 3 keto-petromyzonol sulfate (Li et al. Science 296: 138-142 (2002)) and/or L-arginine (a potent odorant and likely feeding attractant). They can be used with a variety of liquid carriers such as organic liquids (e.g., alcohols) and/or water, which may or may not be buffered. They may be adsorbed onto an inert carrier, such as firebrick, charcoal, silica, alumina, or talc, for example.

Compounds of the present invention can be incorporated into a polymer matrix or onto a solid support. Exemplary such materials include polycaprolactone, polylactide, polydimethylsiloxane, liposomes, silica gel, sand, charcoal or other forms of carbon, alumina, and firebrick.

Compounds of the present invention can be used with a variety of additives including other pheromones (e.g., 3-ketopetromyzonol sulfate and related compounds) and attractants.

Compounds of the present invention might also be administered in liquid form via pumps (e.g., peristaltic pumps from shore or submersible osmotic pumps like Alzet minipumps). Current methods of lamprey control include fluid addition of lampricides by peristaltic pumps. Implantable minipumps are used to slowly deliver drugs to laboratory animals. They have capacity to pump their contents at various metered rates for weeks. This means they can function unattended throughout the length of a typical lamprey spawning period and release controlled levels of pheromone solution.

Compounds of the present invention may also be used in traps for trapping lampreys. Traps that might be used with pheromones include: two-compartment traps (Purvis et al., *Great Lakes Fishery Commission Technical Report* (1985)), portable assessment traps Schuldt et al. *Progressive Fish Culturist*, 44:4,220-221 (1982)), traps mounted in barrier systems, submerged funnel traps (Morris and Maitland, *Journal of Fish Biology*, 31:513-516 (1987)), fyke nets, fish wheels, steel cages, pound nets, and others, some which may be custom modified.

The presence of compounds of the present invention may also be measured in river water to assess larval population size. Water samples could thus be sampled, and the concentrations of pheromone measured therein correlated with population density. This might be accomplished in several manners as follows.

ELISA assays could be developed with the help of an antigen that could be produced from synthetic derivatives of 2 or 3. An ELISA assay could be used to quantify the larval population (currently a large amount of money is spent trying to determine these numbers). This approach has been described in some detail for the sea lamprey sex pheromone (U.S. Pat. Publication No. 2003/0108583 and U.S. Pat. No. 5,620,845).

Mass spectrometric assay: Synthetic or naturally isolated 1, 2 or 3 could be used to create standard curves useful in quantifying low levels of 1, and/or 2 and/or 3 in river and larval holding waters after they had been removed and purified from these waters using C18 or other resins and HPLC. Partially purified river or larval holding water samples might also be assayed by adding various amounts of 1, 2, and/or 3 to them to establish internal standards, allowing quantification by fitting a regression curve with the intercept representing that quantity of the compound of interest naturally found in the sample. Thus, river waters might be obtained from various streams suspected of having larval populations and assayed to determine whether chemical treatment might be required or whether one might expect them to attract adults. Larval holding waters being used a source of compounds of the present invention could also be assayed in this manner to determine cue production.

HPLC separation of fluorescent derivatives of 2 or 3 to quantify river water concentrations: Pure samples of 2 or 3 can be chemically modified to produce derivatives that can be detected at very low concentrations. These materials could, in turn, be used to develop methods for quantifying the level of natural 2 or 3 present in river or lake water. This information can be used to assess lamprey larval population.

EXAMPLES

Objects and advantages of this invention are further illustrated by the following examples, but the particular materials and amounts thereof recited in these examples, as well as other conditions and details, should not be construed to unduly limit this invention.

Methods

Animals. Migratory sea lampreys were procured from riverine traps rivers operated by the U.S. Fish and Wildlife Service and the Department of Fisheries and Oceans Canada, and the transported to either Hammond Bay Biological Station (HBBS) for behavioral testing or The University of Minnesota for EOG recording. Larval sea lamprey were captured by electro-shocking in Michigan streams and transported to HBBS where groups of 500 animals were maintained in 200L flow-through tanks with sand for burrowing. They were fed twice weekly by turning off their water and adding baker's yeast to their tanks following established protocols (Polkinghorne et al., *Fish Physiol. Biochem.*, 24, 15-30 (2001)), and a day later resuming flow. Several tanks were maintained as a control; they contained sand, flowing lake water, and had yeast added to them in small quantities.

Collecting, extracting, and fractionating larval water. Water from the tanks described above was collected 24 hours after feeding. For initial screening experiments, 1 liter (1-L) samples of larval holding water was passed through paper-filters (Whatman, Maidstone, England; 1 L/min) and reversed phase C18 solid-phase extraction cartridges (1 L/cartridge/hr; Waters, Milford, Mass.) which had been previously activated by passing 5 ml of methanol through followed by distilled water (Polkinghorne et al., *Fish Physiology and Biochemistry*, 24: 15-30 (2001)). The C18 column was then extracted with 5 ml methanol, dried under a stream of nitrogen, and fractionated on an HPLC equipped with a reversed phase C18 column (Nova-pak C18, Waters Chromatography, Milford, Mass.), using a linear gradient that ran from 15%-100% methanol/water over 60 minutes (min) (3 min/fraction). Fractions of interest were then re-injected onto the HPLC running with a shallower methanol gradient (running from 35% to 65% methanol over the course of an hour at 1 ml/min). The HPLC column was coupled to a mass spectrometer (MS) with an electrospray ionization (ESI) source.

For large-scale isolation, larval lamprey were maintained in the same manner, and their holding water collected following feeding, according to the protocol described above except that water was filtered by passing it through a 75 micron filter cartridge (Hytrex, Osmonics, Inc. Minnetonka, Minn.; 500 ml/min). Filtered larval holding water was then extracted using 1.05 kg of Amberlite XAD7HP (Supelco Inc., St. Louis, Mo.) held in a glass column (120 cm tall, 50 mm in diameter). Prior to extraction, the XAD7HP in this column was washed with 4 liters of methanol (100 ml/min), followed by 4 liters clean lake water (100 ml/min). For pheromone extraction, 700 L of pre-filtered larval holding water was pumped through the column resin at a rate of 500 ml/min using a peristaltic pump (Masterflex Model 7552-02; Cole Parmer, Vernon Hills, Ill.). The XAD7HP resin was next eluted with 4 liters of methanol (100 ml/min) which was subsequently concentrated to 200 ml using a rotary-evaporator (40° C.; 10 mm Hg). For this particular experiment, an additional purification step was included in which 1 ml of extract (representing 1000 L of holding water) was passed through a 50 mm×122 cm glass column containing 100 g SEPHADEX G15 (Amersham Pharmacia Biotech AB, Uppsala, Sweden). Fractions were collected every 8 minutes, and fractions containing pheromones (Compounds I and II) identified using ESI-MS. To purify these compounds still further, additional HPLC fractionation. HPLC fractionation employed the same protocol described in the previous paragraph except that more concentrated aliquots of extract were injected (quantities derived from 200 L of larval holding water). Fraction/compound purity and quantity was determined using NMR and by drying down and weighing individual samples.

Using electro-olfactogram recording (EOG) to screen for olfactory activity. The EOG measures extracellular voltage transients believed to reflect large numbers of olfactory receptor generator potential (Sorensen et al. in: *The Physiology of Fishes*, 2$^{nd}$ ed., (ed., R. E. Evans), 375-406, (CRC Press, FL, 1998)). To accomplish EOG recording, freshly-captured migratory adult sea lamprey were anesthetized, immobilized, and their olfactory epithelium exposed following established protocols (Li et al., *J. Gen. Physiol.*, 105, 569-589 (1995); and Li et al., *Petromyzon marinus, J. Comp Physiol. A.*, 180, 429-438 (1997)). One electrode was placed on the head and the other positioned to find a region of maximum sensitivity to our standard, $10^{-5}$ M L-arginine. Test odorants were then pulsed over the nose for 3-sec intervals with breaks. All stimuli were tested at least twice. Aliquots of appropriate solvents were diluted and tested as controls.

Confirming biological activity using a behavioral assay. Migratory sea lampreys were tested at night in large (9×1.8 meters (m)) 2-choice mazes supplied with natural lake and rivers waters (400 L min$^{-1}$) designed to simulate the scenario of lamprey encountering a river plume in a lake. Test odors were pumped down one side (in a way shown by dye to effect complete mixing) and appropriate controls (carriers, etc.) down the other. Trials lasted 15 min and commenced when groups of 4 sea lamprey were released from the upstream section of the maze and the time they spent in the stimulus side or its control noted. Experiments typically employed 14 trails and were evaluated by t-test after arc-sign transformation (Vrieze et al., *Can. J. Fish. Aquat. Sci.*, 58, 2374-2385 (2001)).

Identification of components using mass spectrometry (MS) and nuclear magnetic resonance (NMR) spectroscopy. ESI-MS and ESI-MS/MS were performed on an ion trap mass spectrometer (LCQ Classic, Finnigan, San Jose, Calif.). It was operated in the negative ion mode with a spray voltage of 5 kV, sheath gas was 99% pure nitrogen at 60 psi, and sheath fluid was 50:50 20 mM triethylamine:acetonitrile [v/v]. For MS/MS, 30% collision energy was used. High resolution MS was performed in the negative ion mode on a QSTAR mass spectrometer with an ESI-source and a hybrid quadrupole-TOF detector (Applied Biosystems, Foster City, Calif.). Ions of taurocholic acid were used for instrument calibration. $^1$H NMR spectra were recorded at 500 or 800 MHz in CD$_3$OD (or, in the case of 1, 3:1 C$_6$D$_6$:CD$_3$OD) solution.

Results

Figure 1B:
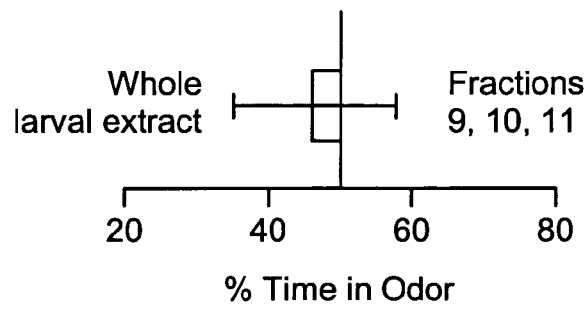

The entire pheromone (all behavioural activity) from larval holding water was concentrated by passing it through C18 or XAD resins and eluting with methanol (see Methods). An extensive regimen of isolation and purification was developed to yield individual chemical constituents. This protocol involved concentrating larval holding water and multiple rounds of fractionation guided by ESI-MS and electrophysiological (EOG) recording from the olfactory system to screen for odorants, followed by behavioural monitoring to confirm behavioural activity. EOG activity of fractions from an intermediate stage of purification is shown in FIG. 1a. This particular step consistently yielded three fractions which, when tested as a mixture, accounted for all behavioural activity in holding water (FIG. 1b). Additional fractionation eventually lead to the isolation of three compounds with olfactory and behavioural activity, and which accounted for all activity found within the fractions they came from.

Seeking the identity of these compounds, 8,000 L of water from 35,000 larvae was fractionated, yielding the same three compounds in 0.1 to 0.7 mg quantities and 95+% purity. The least abundant was identified as petromyzonol sulfate (1) based on its HPLC retention time (vs. a synthetic standard; Toronto Research Chemicals, Canada), fragmentation patterns (ESI-MS-MS), and EOG cross-adaptation (which examines whether compounds bind to the same olfactory receptor(s)). Because 1 was present in such small quantities, a synthesized standard was used to confirm its activity. While its EOG threshold ranged below $10^{-12}$ M (consistent with previous studies (Li et al., *J. Gen. Physiol.*, 105, 569-589 (1995))), it had only weak and somewhat inconsistent behavioral activity even at $10^{-11}$ M (FIG. 2a). Apparently, 1 plays only a minor role in the pheromone activity.

Figure 3A:
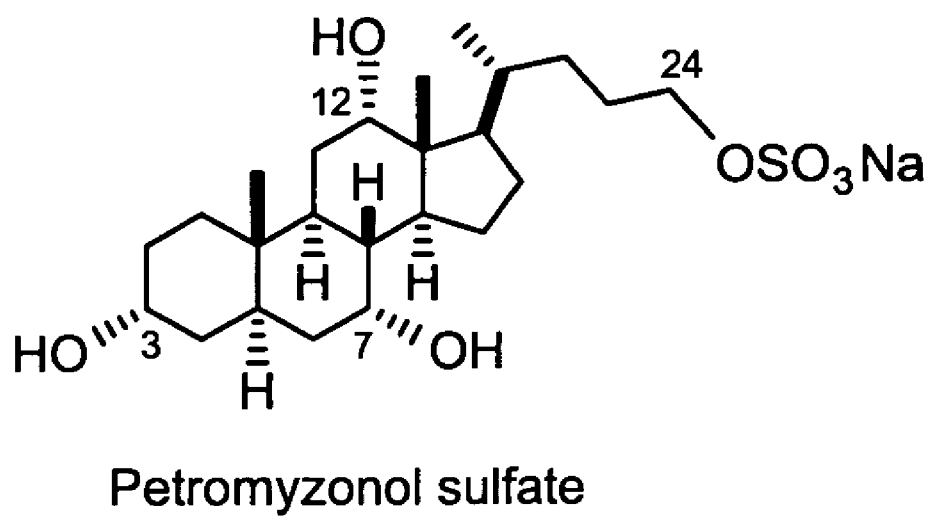
FIG. 3. NMR spectra of compounds examined to effect identification Of the pheromone. All spectra were recorded at 500 MHz; resonances at δ 3.31 and 4.90 ppm and at 3.34 arise from $CD_3OD$ and $CH_3OD$, respectively; • denotes impurity resonances; in spectra a) and d) the regions downfield (left) of the squiggle (δ 1.45 ppm) have their vertical scales increased approximately 1.5× relative to the upfield (right) regions. (a) Expansion of the carbinol methine resonances for petromyzonol sulfate ((1), $C_6D_6/CD_3OD//2/1$, 2:1), from which the number of adjacent (vicinal) protons can be deduced (cf., shapes of δ 3.86 vs. 3.99 ppm resonances in spectra a) vs. b). (b) Petromyzosterol disulfate (2, $CD_3OD$). (c) Petromyzonamine disulfate (3, $CD_3OD$); *indicates a resonance for which there is a match in the spectrum of squalamine.
Figure 3A:
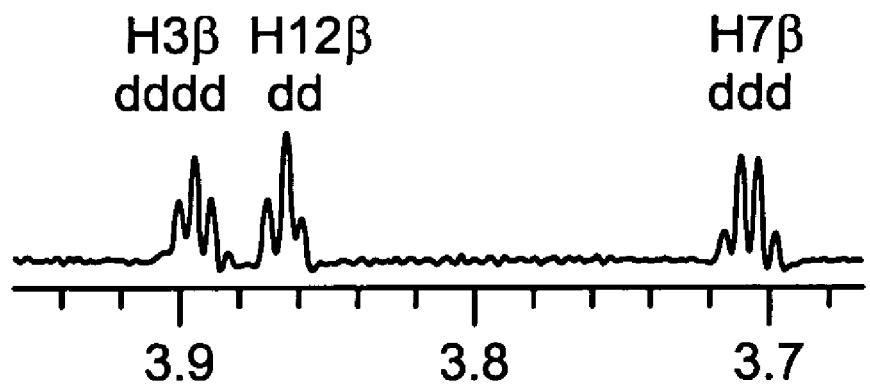

The second most abundant component had a mass of 590 amu (high resolution negative ion ESI-MS). When tested in the behavioural assay, it was consistently attractive at $10^{-11}$ M while EOG recording found it to be detected down to $10^{-12}$ M (FIG. 2b). MS peaks at 589 and 294 in the negative ion mode suggested at least two protic functional groups and MS-MS described at least one sulphate group. Together with its molecular ion isotope distribution pattern, these data suggested a formula of C$_{28}$H$_{46}$O$_9$S$_2$. Proton nuclear magnetic resonance ($^1$H NMR) data (1D (FIG. 3) and gCOSY) next permitted the deduction of structure. Methyl resonances in the 0.7-1.1 ppm region of its spectra (characteristic of steroids) and downfield resonances (3.9-5.5 ppm) indicating protons attached to heteroatom-bearing carbons and/or alkenes (FIG. 3a). Spectral pattern matching (Higashibayashi et al., *J. Am. Chem. Soc.*, 125, 14379-14393 (2003)) led to the hypothesis that these were features in an AB-ring portion, which were confirmed by comparing it with the spectrum of cholesterol sulfate. The sidechain structure of this unknown (C20-C27) was assigned by comparing it with other sulfated (24S)-ergost-22-en-24$^1$-ols (De Marino et al., *Asteriidae. J. Nat. Prod.*, 61, 1319-1327 (1998); Iorizzi et al., *J. Nat. Prod.*, 58, 653-671 (1995); and Iorizzi et al., *J. Nat. Prod.*, 57, 1361-1373 (1994)). Comparing the methine resonance at 3.99 ppm with the set of three methine protons for 1 (FIG. 3c) allowed the assignment of the final site of oxygenation in this compound; namely, a 12-alpha-hydroxy group gives rise to a doublet of doublet (dd or apparent triplet) because of the two adjacent (vicinal) protons (rather the ddd or dddd for the H7 or H3 resonances observed for 1. The COSY spectrum of this compound was consistent with these assignments. This novel and potent steroid is petromyzosterol disulfate (2).

The third component appears to be the most important. It strongly attracted sea lamprey at both $10^{-13}$ and $10^{-12}$ M (although not as strongly as larval water suggesting a synergism with other components) and stimulated EOG responses at concentrations ranging down to $10^{-13}$ M (FIG. 2c). This threshold is adequate for lamprey to detect compound estimated present in river waters based on release rates. Various MS experiments showed indicated two protic groups (peaks at 703 and 351), two sulphate groups, and a mass of 703.3635, consistent with the formula C$_{34}$H$_{60}$N$_2$O$_9$S$_2$. The presence of two nitrogens lead us to examine a variety of aminosterols including squalamine (Moore et al., *Proc. Natl. Acad. Sci. USA*, 90, 1354-1358 (1993)) and congeners (Rao et al., *J. Nat. Prod.*, 63, 631-635 (2000)). These sulfated steroids are produced by the dogfish shark, another ancient vertebrate, and contain polyamines including spermidine attached at the 3-beta position. Comparing $^1$H NMR spectral data for squalamine with those of the unknown indicated a nearly identical pattern of chemical shifts for all 16 protons in the C20-C27 sidechain portion. However, the remaining downfield resonances (2.2-4.5 ppm) showed differences in chemical shifts vs. squalamine. Accordingly, it was deduced that the C7 axial hydroxyl (ddd, cf. H7-beta in 1, FIG. 3a) is sulfated and an unorthodox amino-containing substituent resides at C3. To account for the features of that C3-sidechain (two remaining units of unsaturation, a $C_7H_{13}N_2O$ moiety, and two isolated tri-methylene —$(CH_2)_3$— spin systems (revealed by gCOSY)), it was proposed that an N-(3-aminopropyl) pyrrolidinone subunit, an apparently unprecedented element for a natural product. This assignment has been supported through synthesis (from 5-alpha-cholestan-3-one) of a simple analog containing this 3-beta-amino substituent and observing that the patterns of $^1$H NMR spectra. Although it has not yet been possible to collect $^{13}$C NMR data because of limited sample, full synthesis has commenced and is providing validation. This compound is petromyzonamine disulfate (3).

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. An isolated or chemically synthesized compound having the formula (Formula II):

Formula II wherein:

wherein:
q is 0;
p is 0 or 1;
n is 2 or 3;
k is 0;
X is —N(H)— or —C(O)N(H)—;
Z is O;
$R^{2'}$ and $R^{3'}$ are independently selected from the group consisting of H, —OH, and —OSO$_3$M;
$R^{4'}$ is H, an alkyl having six carbons or less, —(CH$_2$)$_r$OH, or —(CH$_2$)$_r$OSO$_3$M wherein r is 0, 1, or 2;
$R^{5'}$ is —OH, —OSO$_3$M, —CH$_2$OH, or —CH$_2$OSO$_3$M; and
M is a Na counterion;
Y is —O—, —N(H)—, or —N(R$^{8'}$)—;
$R^{8'}$ is a branched or unbranched alkyl or a cycloalkyl;

$\sim\!\!\sim$ represents a single or double carbon-carbon bond between C4 and C5 or C5 and C6;

$\sim\!\!\sim$ represents a single, double, or a triple carbon-carbon bond between C22 and C23;

$\xi$ at C3, C5, C7, C12, C20, and C24 represents a bond to the attached substituent that is either in front of (β) or behind (α) the plane of the paper, and defines the R or S absolute configuration of the carbon atom that bears the attached substituent;

m is 1, 2, 3, or 4;
with the proviso that $R^{1'}$ is not 2-(N-pyrrolidino)ethylamino.

2. An isolated or chemically synthesized compound having the formula (Formula II):

Formula II wherein wherein
q is 0;
p is 0;
n is 2 or 3;
k is 0; X is —N(H)—;
Z is O;
at least one of $R^{2'}$ and $R^{3'}$ is —OH, and —OSO$_3$M;
$R^{4'}$ is H, an alkyl having six carbons or less;
$R^{5'}$ is —OH, —OSO$_3$M, —CH$_2$OH, or —CH$_2$OSO$_3$M; and
M is a Na counterion;
Y is —O—, —N(H)—, or —N(R$^{8'}$)—;
$R^{8'}$ is a branched or unbranched alkyl or a cycloalkyl;

represents a single or double carbon-carbon bond between C4 and C5 or C5 and C6;

represents a single, double, or a triple carbon-carbon bond between C22 and C23;

at C3, C5, C7, C12, C20, and C24 represents a bond to the attached substituent that is either in front of (β) or behind (α) the plane of the paper, and defines the R or S absolute configuration of the carbon atom that bears the attached substituent;

m is 1, 2, 3, or 4;

with the proviso that $R^{1'}$ is not 2-(N-pyrrolidino)ethylamino.

3. An isolated or chemically synthesized compound having the formula:

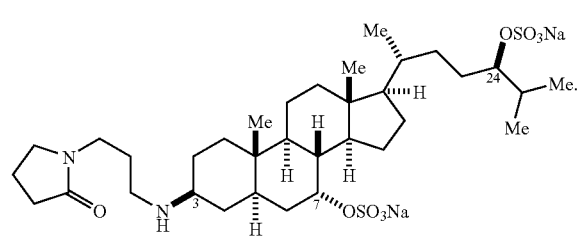

Petromyzonamine disulfate (3)

4. A solid form of a compound having the formula:

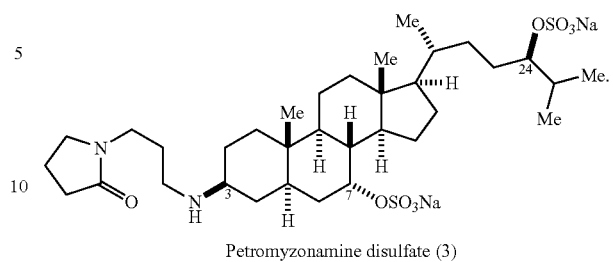

Petromyzonamine disulfate (3)

5. A lamprey attractant composition comprising a carrier and a compound having the formula:

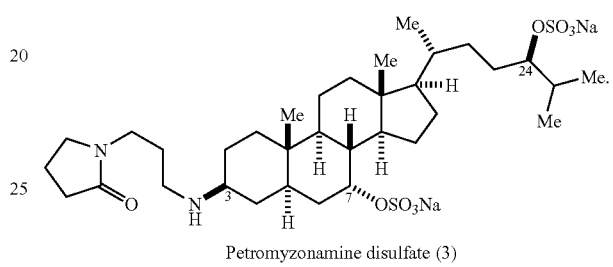

Petromyzonamine disulfate (3)

* * * * *